United States Patent
Zhang et al.

(10) Patent No.: US 10,788,486 B2
(45) Date of Patent: Sep. 29, 2020

(54) GRAPHENE OXIDE-BASED NANOLAB AND METHODS OF DETECTING OF EXOSOMES

(71) Applicants: The University of Kansas, Lawrence, KS (US); Kansas State University Research Foundation, Manhattan, KS (US)

(72) Inventors: Peng Zhang, Lawrence, KS (US); Yong Zeng, Olathe, KS (US); Mei He, Manhattan, KS (US)

(73) Assignees: The University of Kansas, Lawrence, KS (US); Kansas State University Research Foundation, Manhattan, KS (US)

( * ) Notice: Subject to any disclaimer, the term of this patent is extended or adjusted under 35 U.S.C. 154(b) by 28 days.

(21) Appl. No.: 15/728,155

(22) Filed: Oct. 9, 2017

(65) Prior Publication Data

US 2018/0100853 A1    Apr. 12, 2018

Related U.S. Application Data

(60) Provisional application No. 62/405,927, filed on Oct. 9, 2016.

(51) Int. Cl.
*G01N 33/543* (2006.01)
*B01L 3/00* (2006.01)
*G01N 33/68* (2006.01)

(52) U.S. Cl.
CPC .. *G01N 33/54393* (2013.01); *B01L 3/502707* (2013.01); *B01L 3/502761* (2013.01);
(Continued)

(58) Field of Classification Search
CPC ....... G01N 33/54393; G01N 33/54353; G01N 33/6872; G01N 33/54326; B01L 3/502761; B01L 3/502707
See application file for complete search history.

(56) References Cited

U.S. PATENT DOCUMENTS

2010/0285573 A1* 11/2010 Leck ............... B01L 3/5088
                                                   435/288.4
2012/0220053 A1*  8/2012 Lee ................ H01L 29/78696
                                                   436/501
(Continued)

OTHER PUBLICATIONS

Xu et al., Dopamine-Induced Reduction and Functionalization of Graphene Oxide Nanosheets, Macromolecules, vol. 43, pp. 8336-8339. (Year: 2010).*
(Continued)

*Primary Examiner* — Melanie Brown
(74) *Attorney, Agent, or Firm* — Hovey Williams LLP

(57) ABSTRACT

A capture device for capturing a biological substance can include: a substrate; a graphene-oxide layer on the substrate; at least one polydopamine polymer coupled with the graphene-oxide; and at least one targeting receptor coupled to the polydopamine(s), wherein the targeting receptor is capable of targeting/binding with a target biological substance. The graphene-oxide may be covalently coupled with the substrate and polydopamine, and the polydopamine may be covalently coupled with the targeting receptor. The targeting receptor can be an antibody or fragment thereof. The target biological substance can be an exosome. The substrate can be a particle (e.g., magnetic, such as magnetically responsive) or a surface in a microfluidic channel. The surface can be a top surface of a post, the post having a Y-shaped cross-sectional profile. In one aspect, the substrate is a particle. The capture device can include the target biological substance bound to the targeting receptor.

19 Claims, 16 Drawing Sheets

(52) U.S. Cl.
CPC . *G01N 33/54326* (2013.01); *G01N 33/54353* (2013.01); *G01N 33/6872* (2013.01); *B01L 2200/0631* (2013.01); *B01L 2200/0647* (2013.01); *B01L 2300/0636* (2013.01); *B01L 2300/0816* (2013.01); *B01L 2300/0887* (2013.01)

(56) References Cited

U.S. PATENT DOCUMENTS

| | | | | |
|---|---|---|---|---|
| 2014/0154770 | A1* | 6/2014 | Vittadello | G01N 33/551 435/177 |
| 2015/0024961 | A1* | 1/2015 | Klass | C12Q 1/6886 506/9 |
| 2015/0285808 | A1* | 10/2015 | Nagrath | G01N 33/54366 435/7.23 |
| 2017/0074871 | A1* | 3/2017 | Campbell | B01L 3/502792 |

OTHER PUBLICATIONS

He et al. The attachment of Fe3O4 nanoparticles to graphene oxide by covalent bonding, Carbon, vol. 48, pp. 3139-3144. (Year: 2010).*

Peng et al. Label-free electrochemical immunosensor based on multi-functional gold nanoparticles-polydoamine-thionine-graphene oxide nanocomposites film for determination fo alpha-fetoprotein, Journal of Electroanalytical Chemistry, vol. 712, pp. 89-95. (Year : 2014).*

Zhang, P. et al., "Ultrasensitive microfluidic analysis of circulating exosomes using a nanostructured graphene oxide/polydopamine coating", The Royal Society of Chemistry (Mar. 22, 2016), DOI: 10.1039/c6lc00279j.

* cited by examiner

GRAPHENE OXIDE-BASED NANOLAB AND METHODS OF DETECTING OF EXOSOMES

CROSS-REFERENCE

This patent application claims priority to U.S. Provisional Application No. 62/405,927 filed Oct. 9, 2016, which provisional is incorporated herein by specific reference in its entirety.

STATEMENT REGARDING FEDERALLY SPONSORED RESEARCH

This invention was made with government support under contracts R21 CA186846 and P20 GM103418 awarded by the National Institutes of Health. The government has certain rights in the invention.

BACKGROUND OF THE DISCLOSURE

Exosomes of 30-150 nm in size are secreted by most eukaryotic cells, and have been recently identified as key mediators in many cellular processes, such as cell communication and immune response. Exosomes are actively secreted in cancer and enriched in a set of biomolecules reflecting the states of the cells of origin. Thus, targeting exosomes could provide a promising tool for tumor biology and early disease detection without invasive biopsy. However, isolation and analysis of exosomes is still very challenging. Standard ultracentrifugation isolation is time-consuming and yields low recovery and low purity. Conventional tools for exosome analysis, such as Western blot and enzyme-linked immunosorbent assays (ELISA), are limited by low sensitivity, lengthy processes, and high sample demand. These technical challenges severely constrain the extensive biomedical studies of exosomes.

Nanomaterials are rapidly evolving as enabling interfaces for bioanalysis. Recently, graphene nanomaterials have gained increasing interests for biosensing due to their exceptional optical, electronic, and structural properties (e.g., unsurpassed specific surface area). However, there remains a need for improved approaches and devices for exosome analysis.

SUMMARY OF THE DISCLOSURE

In one embodiment, a capture device for capturing a biological substance can include: a substrate; a graphene-oxide layer on the substrate; at least one polydopamine polymer coupled with the graphene-oxide; and at least one targeting receptor coupled to the at least one polydopamine, wherein the targeting receptor is capable of targeting and binding with a target biological substance. In one aspect, the substrate includes a functional group covalently coupled with a functional group of the graphene-oxide layer. In one aspect, the graphene-oxide layer includes a functional group that is covalently coupled with a functional group of the at least one polydopamine polymer. In one aspect, the at least one polydopamine polymer includes a functional group that is covalently coupled with a functional group of the at least one targeting receptor. In one aspect, the targeting receptor is an antibody or fragment thereof. In one aspect, the target biological substance is an exosome. In one aspect, the substrate is a surface in a microfluidic channel. In one aspect, the surface is a top surface of a post, the post having a Y-shaped cross-sectional profile. In one aspect, the substrate is a particle. In one aspect, the particle is a magnetic particle having a magnetic core and a functionalized shell having a functional group, such as an amine or other that reacts with a carboxylic acid. In one aspect, the capture device can include at least two of the following: the substrate includes a functional group covalently coupled with a functional group of the graphene-oxide layer; the graphene-oxide layer includes a functional group that is covalently coupled with a functional group of the at least one polydopamine polymer; or the at least one polydopamine polymer includes a functional group that is covalently coupled with a functional group of the at least one targeting receptor. In one aspect, the capture device can include the target biological substance bound to the targeting receptor.

In one embodiment, a method of determining whether a target biological substance is present in a sample can include: providing the capture device of one of the embodiments; contacting the sample with the capture device; analyzing the capture device for presence of the target biological substance being bound with the targeting receptor; and determining the presence of the target biological substance in the sample, wherein if the target biological substance binds with the targeting receptor, the target biological substance is present in the sample, or if the target biological substance does not bind with the targeting receptor, the target biological substance is not present (e.g., absent) in the sample.

In one embodiment, a method of capturing a target biological substance can include: providing the capture device of one of the embodiments; and contacting a sample with the capture device such that the target biological substance associates with the targeting receptor. In one aspect, the method can include analyzing the capture device for presence of the target biological substance being bound with the targeting receptor. In one aspect, the method can include one of removing the substrate from the sample; or removing the sample from the substrate. In one aspect, the method can include dissociating the target biological substance from the targeting receptor. In one aspect, the method can include qualitatively or quantitatively determining an amount or relative amount of the target biological substance in the sample. In one aspect, the sample is a biological sample from a subject. In one aspect, the method can include: identifying the presence of the target biological substance in the sample; and determining a disease state in the subject based on the presence of the target biological substance in the sample.

In one embodiment, a method of determining a disease state in a subject can include: providing the capture device of one of the embodiments; obtaining a sample from the subject; contacting the sample with the capture device; analyzing the capture device for presence of the target biological substance being bound with the targeting receptor; determining the presence of the target biological substance in the sample, wherein if the target biological substance binds with the targeting receptor, the target biological substance is present in the sample, or if the target biological substance does not bind with the targeting receptor, the target biological substance is absent from the sample; identifying: presence of the disease state in the subject when the target biological substance is present in the sample, or absence of the disease state in the subject when the target biological substance is absent from the sample; and reporting to the subject the presence or absence of the disease state to the subject. If the subject is diagnosed with the disease state, a medical professional can then recommend a suitable treatment protocol for that disease state. The method can then include the subject undergoing the treatment protocol.

DESCRIPTION OF THE DISCLOSURE

Figure 1:
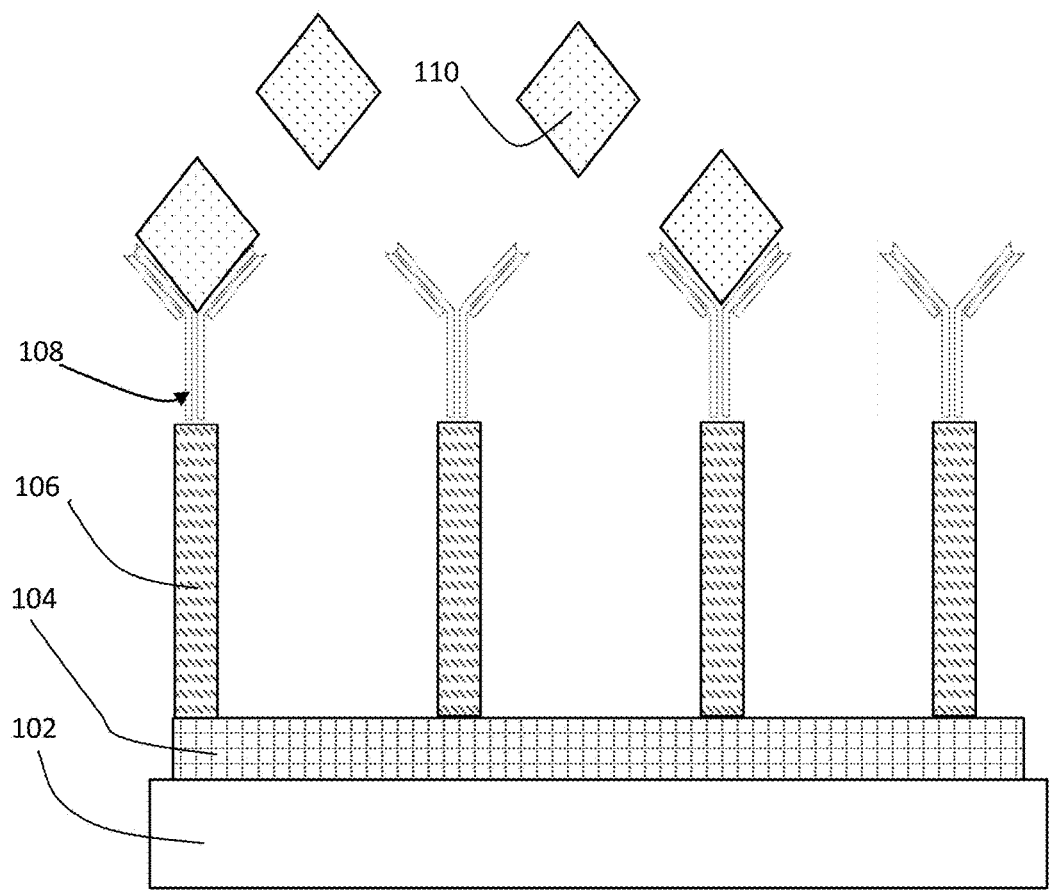
FIG. 1 illustrates an embodiment of a capture device configured to capture ligands, which includes a surface of a substrate that is coated with graphene oxide nanosheets that are coupled with polydopamine having targeting receptors.

Generally, the present technology provides devices, systems and nanostructured coating methods that offer much improved performance to exosome capture, isolation and analysis. In one embodiment, the present technology provides a nano-interfaced microfluidic exosome (nano-IMEX) capture platform based on graphene oxide (GO)-PDA nanomaterial on a substrate surface. The GO is linked to the substrate (e.g., macroscopic, microscopic, nano-scale or other) and has polydopamine (PDA) covalently linked thereto, where the PDA includes a targeting receptor that can bind with a targeted exosome or other biomolecule. While exosomes are described herein, it should be recognized that the targeting receptor can be selected to target any specific targeted biomolecule. In an example, the GO-PDA-receptor can bind with the targeted biomolecule for use in an ultrasensitive exosome ELISA assay.

In one aspect, GO has been found to quench fluorescence and hence has been widely used as a quencher in fluorescence sensing. This fluorescence quenching effect, however, limits broader applications of GO in bioanalysis. To overcome this problem, GO is functionalization based on a bio-inspired polydopamine (PDA) surface chemistry. The GO-PDA can be used in microfluidics. The GO-PDA can be used as a versatile coating strategy for treating magnetic beads surface or other micro-nanoparticle surface. It was observed that microfluidic control of surface dopamine polymerization on a GO film produces a PDA coating with unique nanoscale porous morphology. Such nanostructured GO-PDA interface allows for attachment of the PDA to a targeting receptor (Receptor), such as an antibody that binds with an exosome. The GO-PDA-Receptor greatly enhances the efficiency of exosome immuno-isolation, while effectively suppressing non-specific interactions and fluorescence quenching by GO. This nano-interface also allows for use in an ultrasensitive exosome ELISA assay with fluorescence signal amplification. Compared to the existing microfluidic methods and bench-top chemiluminescence ELISA, the GO-PDA-Receptor (e.g., on a particle substrate, or macro substrate such as a chip substrate) improves the detection sensitivity by ~$10^2$ and $10^4$ folds, respectively, and greatly expands the dynamic range. This platform was applied to discriminate ovarian cancer patients from healthy controls by sensitive, specific and rapid detection of targeted exosomes directly from plasma of minimal volume (2 µL) without sample processing. These results demonstrate the potential of the GO-PDA-Receptor platform for exosome research and clinical disease diagnosis and treatment. Thus, in embodiments, the technology encompasses a graphene-based sandwich exosome immunoassay assisted by enzymatic fluorescence signal amplification that also uses PDA as a nano-bio interface.

An embodiment of a capture device can be configured to capture ligands, which includes a surface of a substrate that is coated with graphene oxide nanosheets that are covalently coupled with polydopamine having targeting receptors that can be used for sandwich ELISA of exosomes with enzymatic fluorescence signal amplification.

In one embodiment, a device, system or method of this disclosure does not employ ortho-phenylamine.

An embodiment of the capture device 100 is depicted in FIG. 1. The capture device 100 includes a substrate 102 at least partially coated with a GO layer 104 that is covalently linked to PDA 106 and covalently linked to the targeting receptor 108 (e.g., antibody). The targeting receptor 108 is shown to target a biomolecule 110 (e.g., exosome). This capture device 100 may include a substrate 102 that is a macro-substrate or a particle or bead (e.g., microscopic, nano-scale or other), which particle or bead may or may not be magnetic. The spaces between the PDA 106 can be pores, such as micro-pores or nano-pores, which provides a unique morphology for capturing the biomolecules 110.

Figure 1C:
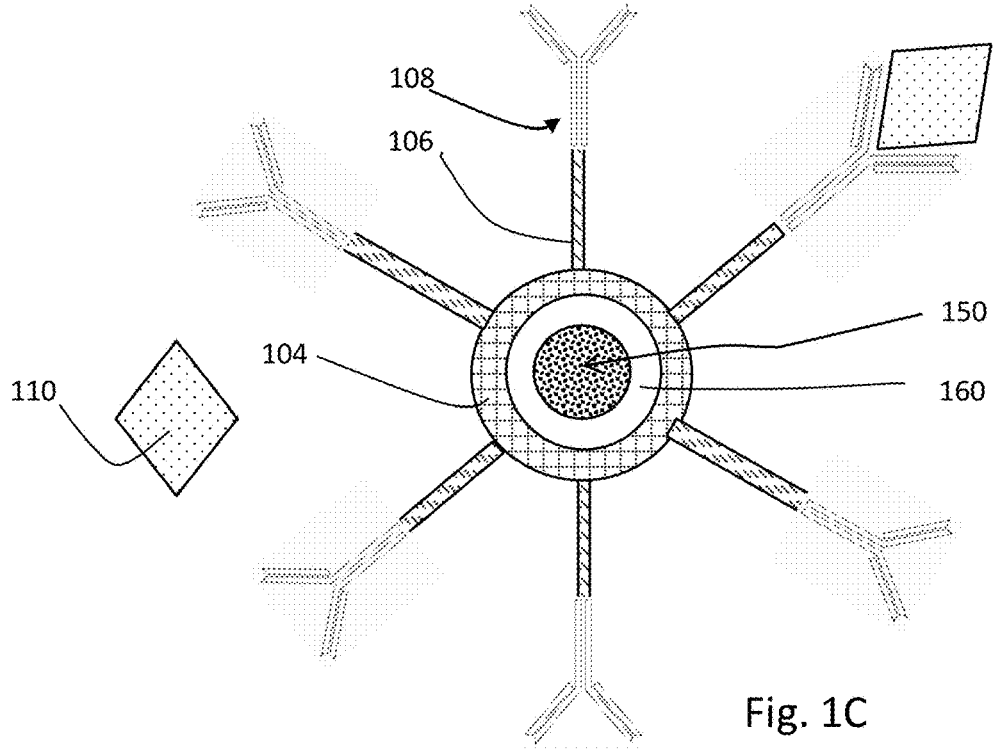
FIG. 1C illustrates an embodiment of a capture device configured to capture ligands, which includes a surface of a core/shell particle that is coated with graphene oxide nanosheets that are coupled with polydopamine having targeting receptors.

FIG. 1C shows the capture device 100c having the core 150 with a shell 160. The GO layer 104 is coated onto the shell 160. The PDA 106 is coupled with the GO layer 104. The targeting receptor 108 is coupled with the PDA 106. The biomolecule 110 can then associate with the targeting receptor 108. The spaces between the PDA 106 can be pores, such as micro-pores or nano-pores, which provides a unique morphology for capturing the biomolecules 110.

The capture device provides a unique nano-structured morphology that is created through the coating methods described herein. See FIG. 10A. The coating methods can be used to other particles (e.g., spherical, irrecular, or other) or to flat or micro-structured surfaces. The substrates or particles may be magnetic or non-magnetic, magnetically responsive or magnetically non-responsive. In some instances, the parcles may be uniform without a core and shell. In any event, any type of particle can be functionalized with an amine to bond with the carboxylic acids of the GO.

In one embodiment, the present technology includes a graphene-based sandwich exosome immunoassay assisted by enzymatic fluorescence signal amplification that also uses PDA linked to the receptor as a nano-bio interface. Features and various embodiments of components of the embodiments of this technology will be apparent from the description and figures presented herein. In general, the device is used for non-invasive procedures which involve testing samples for use in monitoring the treatment of, and/or diagnosing and/or aiding in the diagnosis, of a disorder or condition that is positively correlated with the presence of one or more immunologically detectable markers that are contained within membranous structures, such as exosomes, in a biological sample.

In general, the present disclosure includes obtaining a sample and testing it as generally depicted in FIG. 1. In embodiments, any biological sample can be used, and can be tested directly, or can be subjected to a processing step before being tested. In embodiments, the technology includes the use of a capture device 100 as described further below to detect and/or quantify a complex of detectably labeled antibodies and a target protein that is present in a sample obtained and/or derived from a human subject. In embodiments, the complex is a component similar to the complex formed during a sandwich ELISA assay.

This disclosure includes an illustrative embodiment analysis of exosomes, which generally illustrates the device and sample testing, but the embodiments described in this disclosure can be used and/or adapted for use with any membranous structures that contain immunologically detectable markers. In various embodiments the membranous structures are generally spherical lipid containing bodies. The spherical membranous structure can comprise lipid bilayers. The method is particularly suited for analyzing those membranous structures that are shed or otherwise secreted from cells. Thus, the membranous structures can be derived from any membrane containing biological material, which includes, but is not necessarily limited to, internal cellular membranes, vesicles, such as secretory vesicles, organelles, enveloped structures, plasma membranes and the like. In certain embodiments, the membranous structure is selected from vesicles, exosomes, microvesicles, microparticles, intraluminal vesicles, endosomal derived vesicles, multivesicular bodies, and combinations thereof. In certain approaches, exosomes are characterized by exosome markers, such as D9, CD63, CD81, EpCAM, and combinations thereof.

In embodiments, the marker that is analyzed using a device as further described herein is a protein marker. In embodiments, the protein marker is a cancer marker. In an illustrative embodiment which demonstrates feasibility of applying the present disclosure to a wide range of conditions which are positively correlated with the presence of a protein marker, the disclosure includes a demonstration using a protein marker that is characteristic of ovarian cancer. The disclosure includes a method of diagnosing, or aiding in the diagnosis of or for monitoring the treatment of an individual diagnosed with, suspected of having, or at risk for developing a condition that is positively correlated with a particular protein marker, such as any ovarian cancer marker.

In another aspect, the present disclosure comprises kits. The kits can be provided with the system/device described herein, and can further comprise one or more sealed or sealable containers in which are held reagents for obtaining, processing, and using a biological sample, and/or reagents used to isolate, concentrate and/or purify exosomes. In embodiments, the reagents comprise one or more buffers, such as buffers for mixing with a biological sample and/or separated exosomes. The kits can comprise a capture device or plurality of capture devices having one or more capture agents (e.g., targeting receptors) which include but are not necessarily limited to antibodies and antigen binding fragments thereof. In embodiments, the capture agents comprise antibodies that bind with specificity to the exosome markers CD9, or CD81, or CD63, or Epithelial cell adhesion molecule (EpCAM), or combinations thereof.

Figure 1A:
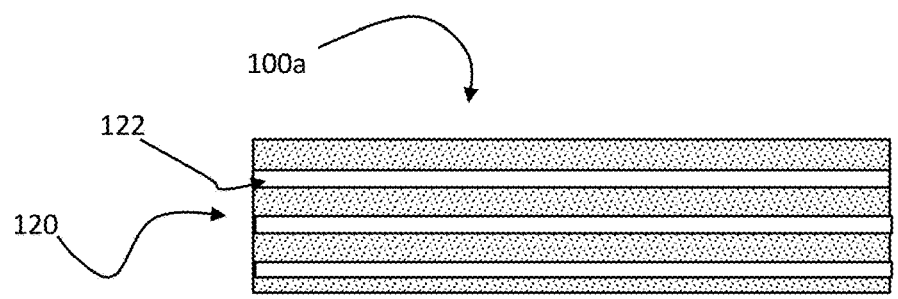
FIG. 1A illustrates an embodiment of a device having a plurality of microfluidic pathways that can be configured as a capture device with a substrate that is coated with graphene oxide nanosheets that are coupled with polydopamine having targeting receptors.

In connection with the drawings and description presented herein, one embodiment of a capture device 100a that has a microfluidic network 120 having one or more microfluidic channels 122 is illustrated in FIG. 1A. While the microfluidic network is shown to be linear, it may be non-linear, curved, branched, or other as common in microfluidic features. The microfluidic network 120 can include the substrate 102 or be the substrate 102. The substrate 102 is linked to the GO, PDA, and targeting receptor as shown and described in connection with FIG. 1.

Figure 1B:
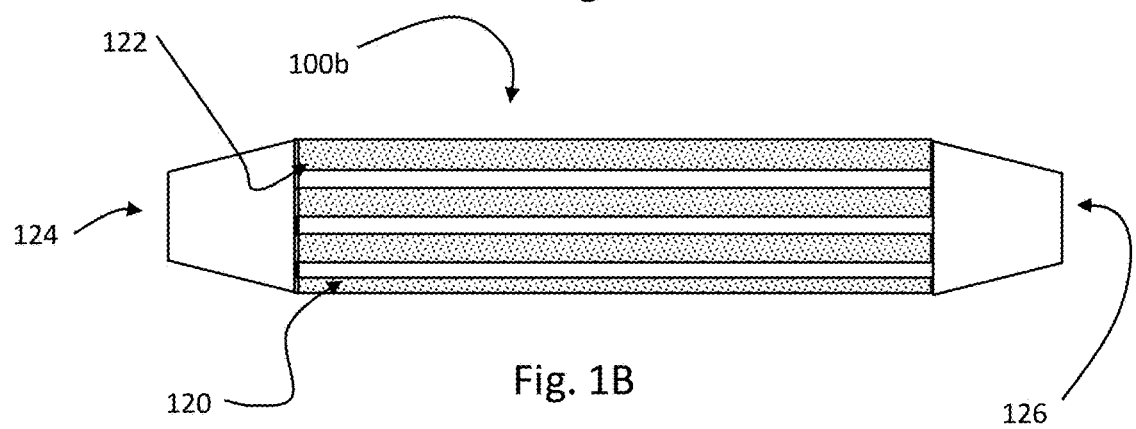
FIG. 1B illustrates an embodiment of a device having an inlet and outlet coupled with a plurality of microfluidic pathways that can be configured as a capture device with a substrate that is coated with graphene oxide nanosheets that are covalently coupled with polydopamine having targeting receptors.

FIG. 1B shows an embodiment of a capture device 100b that has an inlet 124 and outlet 126 fluidicaly coupled through the microfluidic network 120.

Figure 2A:
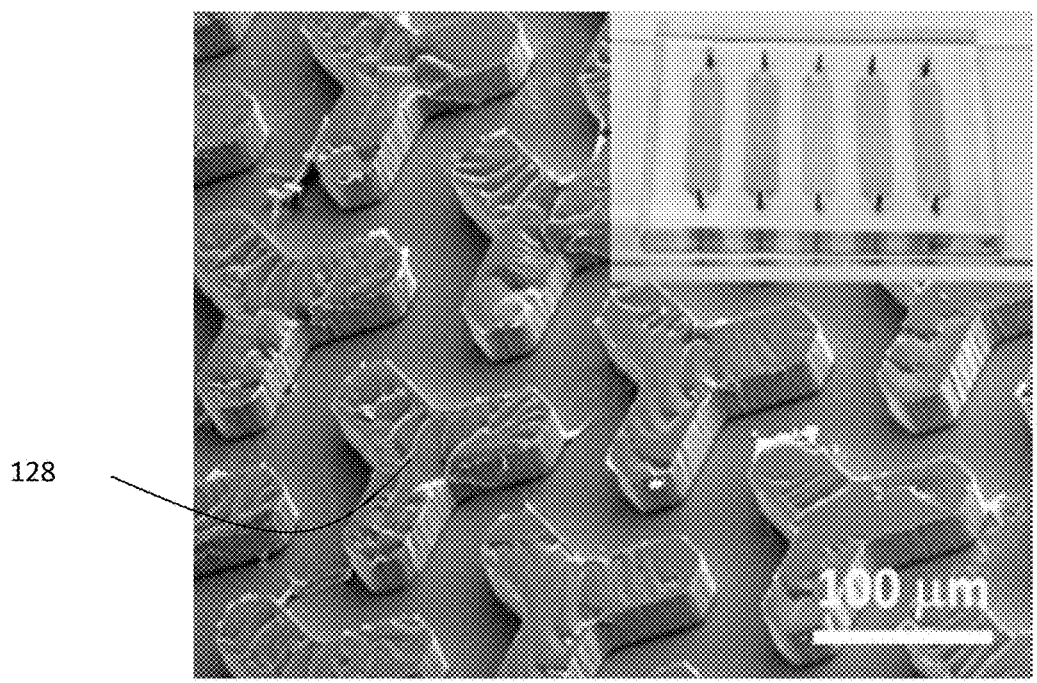
FIG. 2A includes an SEM image of the Y-shaped microposts in a polydopamine-graphene-oxide (GO-PDA) coated chip (inset), with a substrate that is coated with graphene oxide nanosheets that are coupled with polydopamine having targeting receptors.

In one embodiment, the substrate 102 may be Y-shaped, such as shown in FIG. 2A. As such, the microfluidic network 120 may include an array of Y-shaped microposts 128 having the GO-PDA-Receptor (GPR) for capturing exosomes flowing through the channels 122. The chip surface (e.g., substrate) is first silanized or otherwise functionalized so that it can be coated with GO, and then it is coated with a film of GO nanosheets via electrostatic interaction or covalent bonding (e.g., when functionalized with a functional group that reacts with carboxylic acids, hydroxyls or oxirane moieties). The GO coating can be functionalized by bio-inspired polymerization of dopamine under microfluidic control, forming a nanostructured biorecognition interface. Based on this nano-interface, the capture device can be configured as a sandwich exosome ELISA assisted with enzymatic signal amplification.

Figure 5:
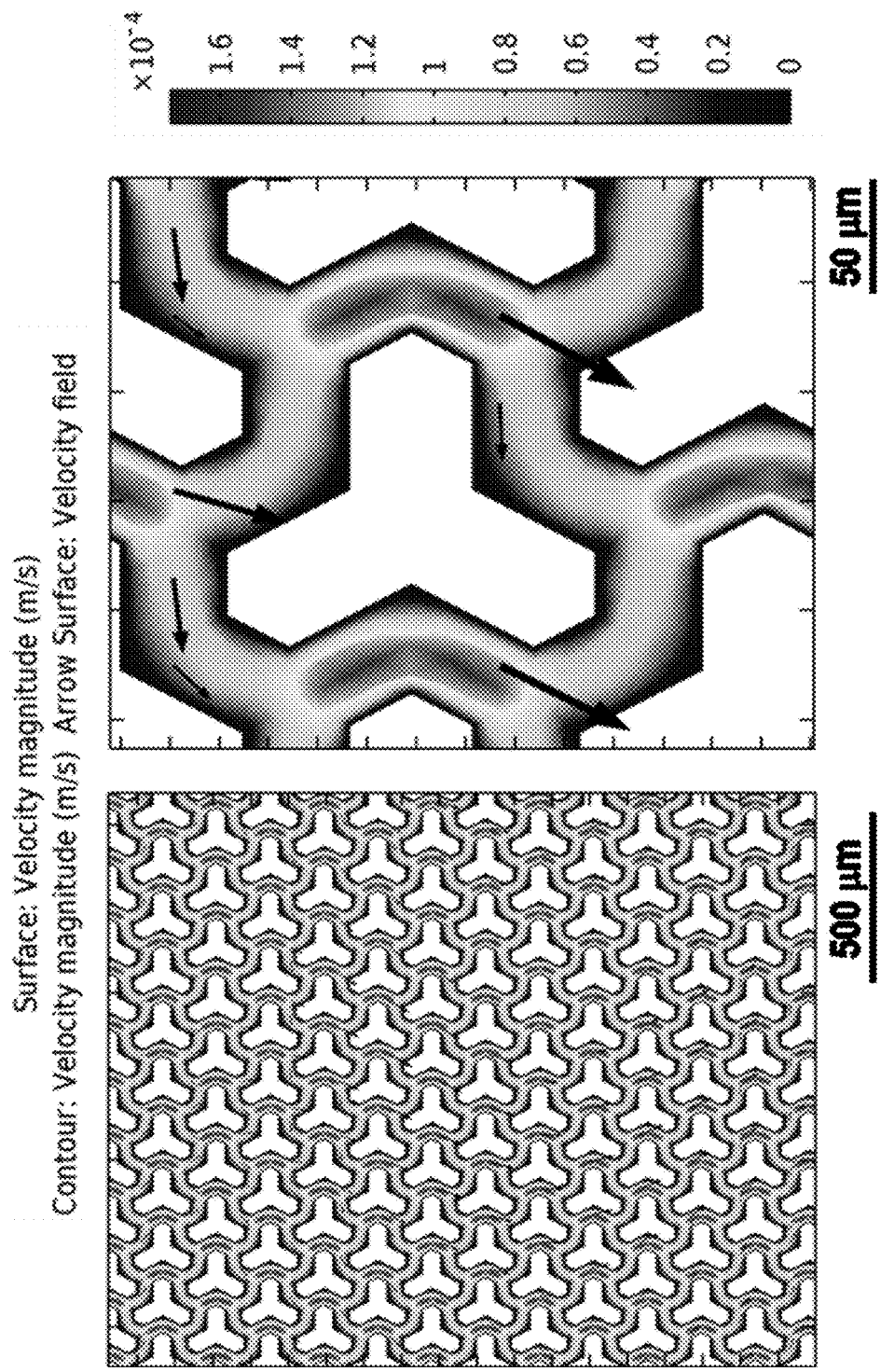
FIG. 5 illustrates finite element simulations of the flow velocity profile inside the Y-shaped micropost array, where the enlarged view to the right shows asymmetric flow bifurcation at the upstream arms of the Y-shaped microposts, as indicated by the length of the arrows that represent overall fluid flow strength across this section of the channel.

FIG. 2A displays the microfabricated array of Y-shaped microposts designed to enhance exosome capture efficiency, compared to the commonly used cylindrical post structure. First, this geometry provides much larger surface area at the same footprint; second, the array constructs a channel network in which a flow is asymmetrically bifurcated and mixed with adjacent streams, as shown by the COMSOL simulation (FIG. 5); lastly, the curved channels defined between the concaved microposts further enhance the mixing efficiency due to the secondary Dean flow.

Figure 2B:
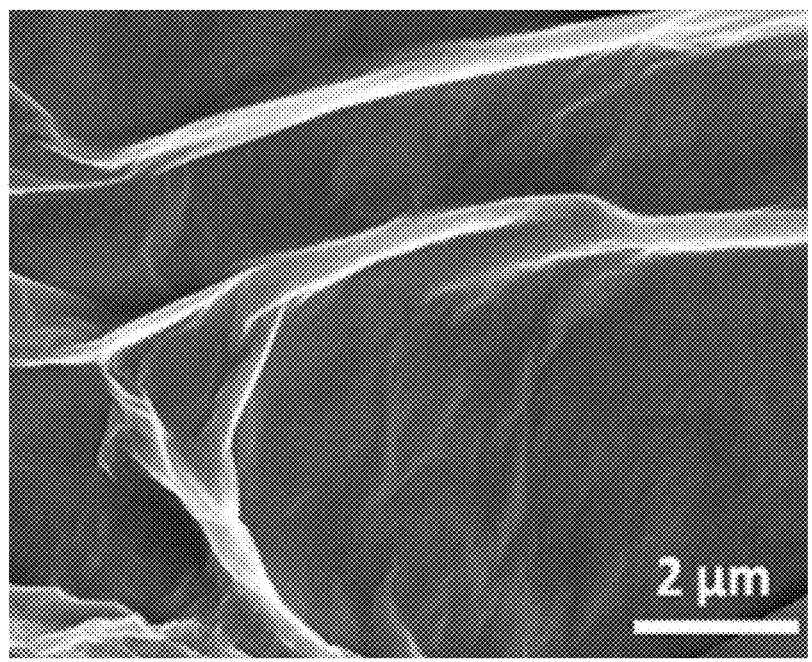
FIG. 2B includes an SEM image of the microscale 3D surface topology formed by GO coating.
Figure 2C:
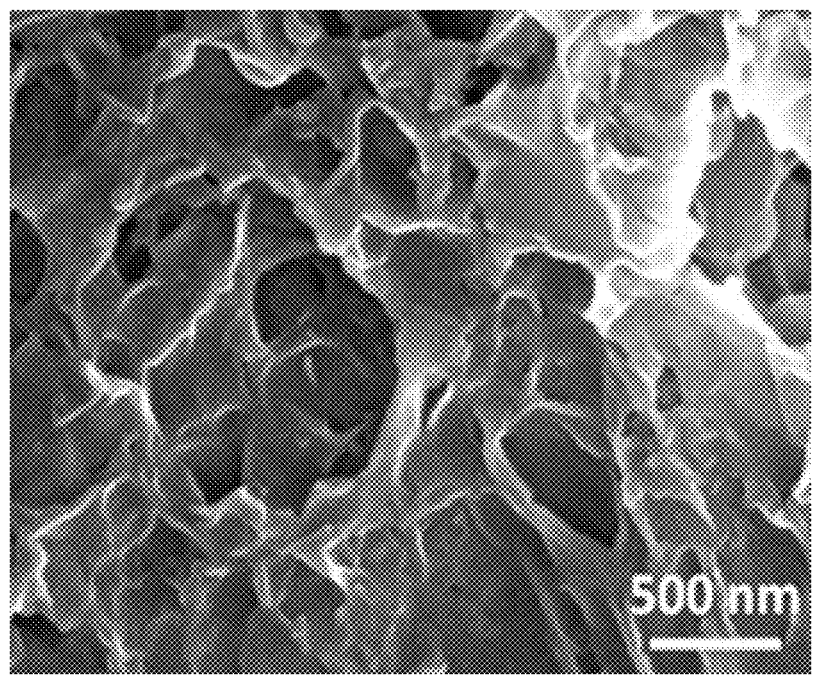
FIG. 2C includes an SEM image of nanoporous PDA film formed on the GO surface.
Figure 6:
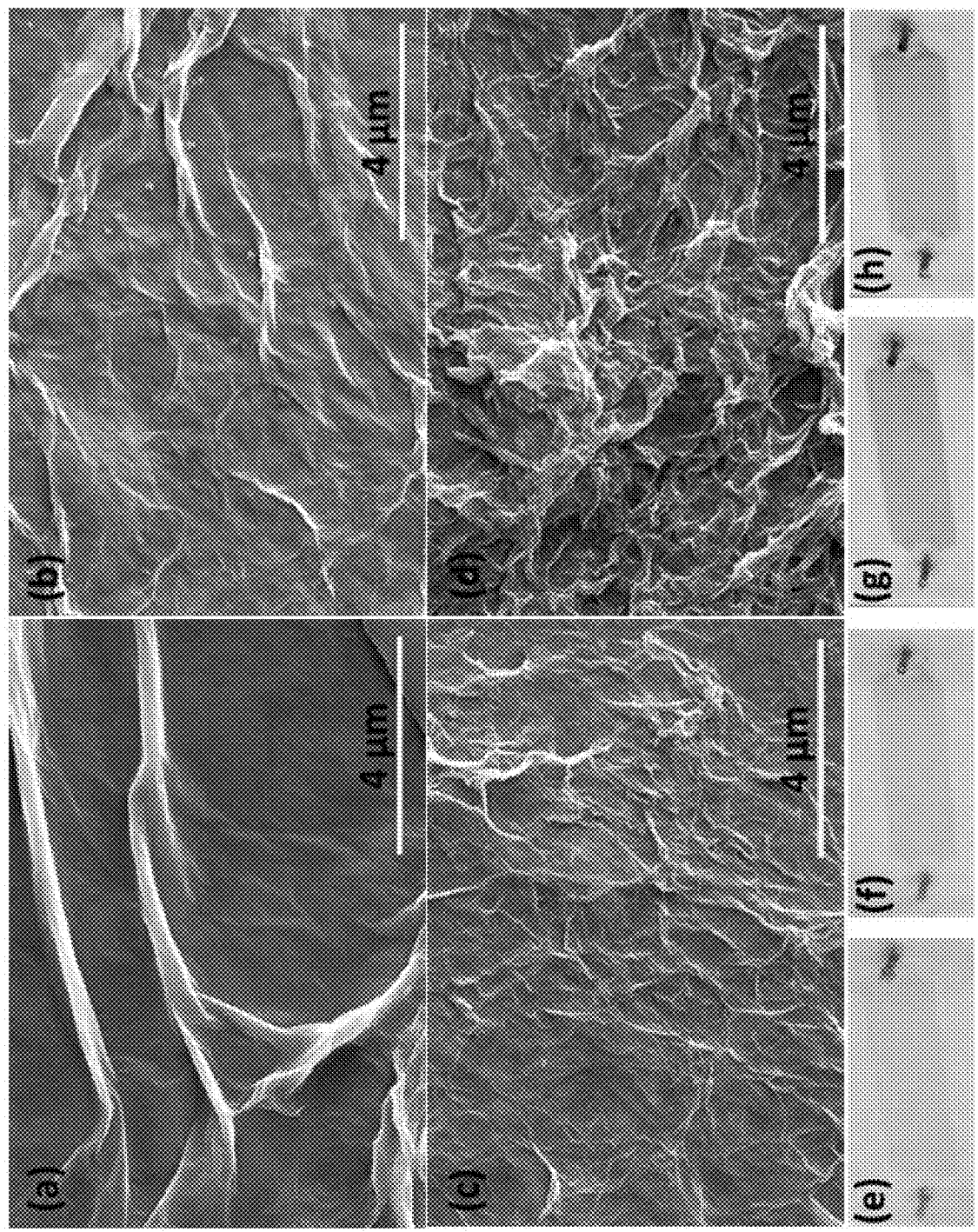
FIG. 6 shows different panels with images of microfluidic PDA functionalization of GO-coated PDMS chip, with SEM images of bare GO layer (Panel a) and a PDA film formed on a GO surface after 1 h (Panel b), 2 h (Panel c) and 3 h (Panel d) reaction, and Panels e-f show corresponding photos of the PDMS microchips used to obtain SEM images in Panels a-d.
Figure 7:
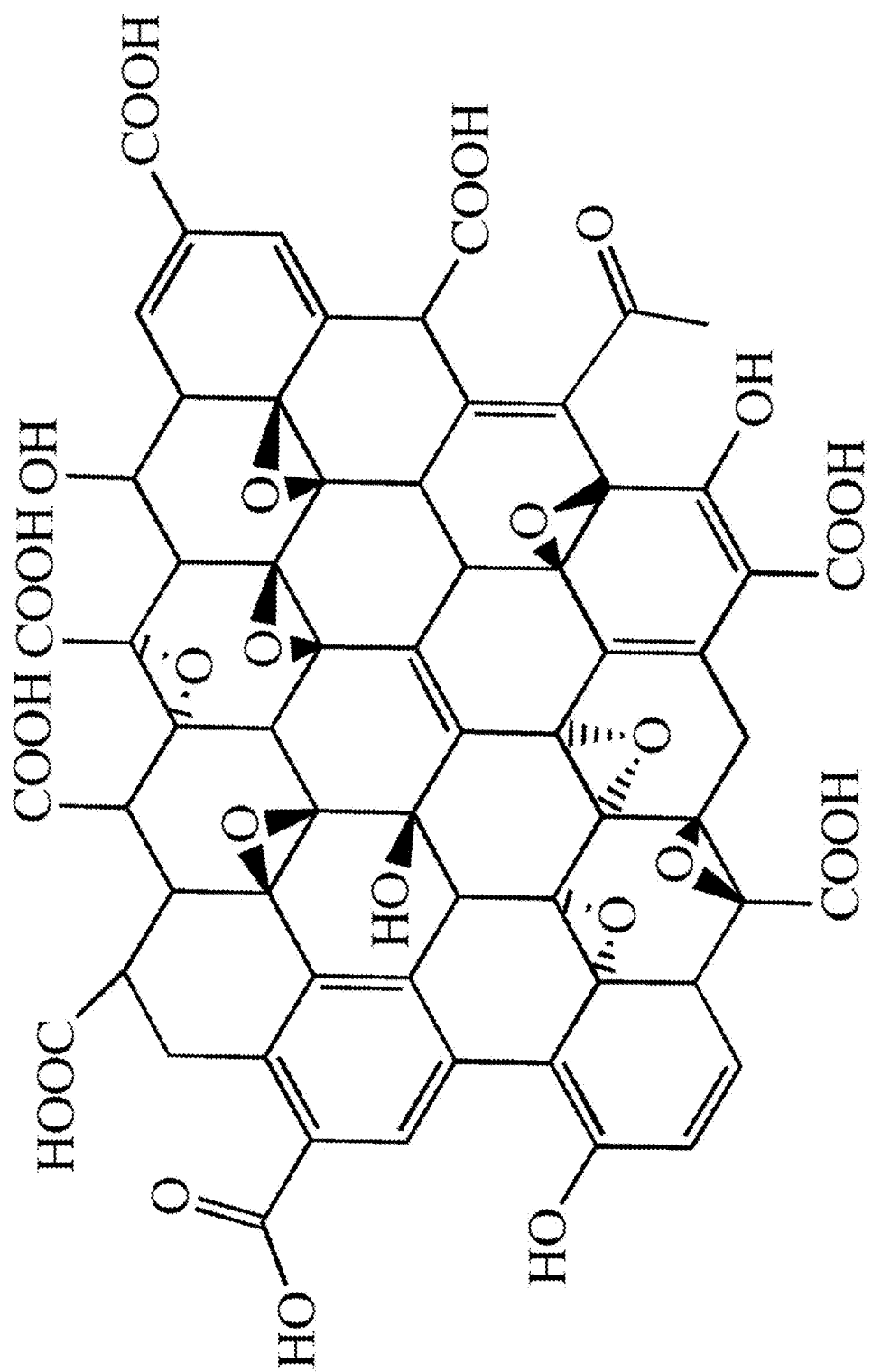
FIG. 7 shows a graphene-oxide chemical structure.
Figure 8:
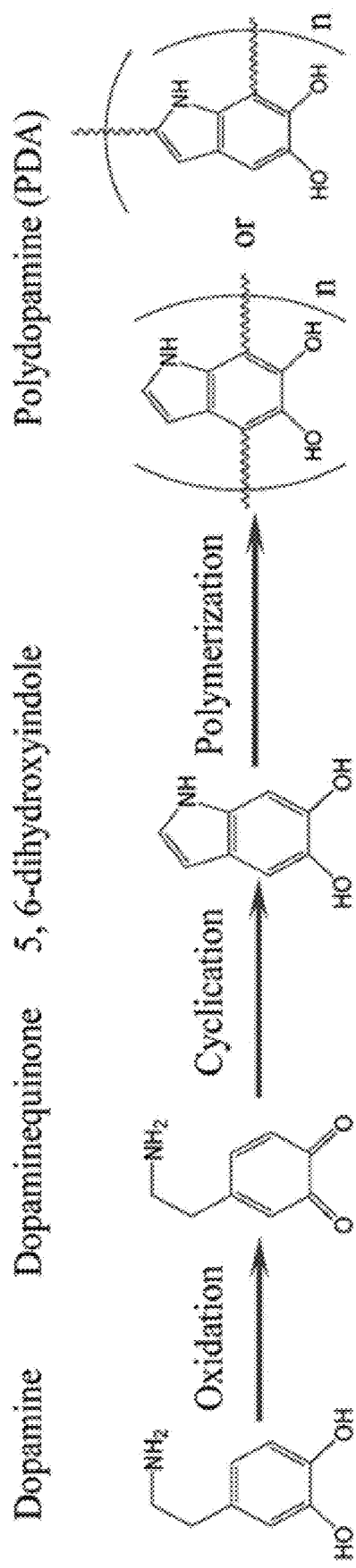
FIG. 8 shows synthesis of polydopamine (PDA) with the two forms, which can be a combination thereof.

To construct the capture device (e.g., nano-IMEX chip (FIG. 2A, inset)), the channel surface was uniformly modified with GO nanosheets, using a simple and robust electrostatic deposition method. As seen in the micrograph of FIG. 2B, the GO coating creates a microscale 3D surface landscape which can significantly enhance the exosome capture efficiency by increasing surface area and creating local fluid mixing. GO is hydrophobic and its fluorescence quenching effect limits the use in fluorescence-based biosensing. Thus, chemical modifications can be used for bioanalysis applications. A single-step microfluidic coating method based on bio-inspired polymerization of dopamine can be used to coat the GO surface with a highly hydrophilic and biocompatible PDA layer. Unlike the benchtop PDA coating, the present method conducts dopamine polymerization under constant laminar flow conditions in microchannels. It was observed that a thin PDA film was initially formed on the GO surface and grew into a three-dimensional monolith-like nanoporous film in 3 hours (FIGS. 2C and 6). The fast deposition kinetics of PDA formed on the surface of GO created an unique 3D monolith-like structure with micro-/nanoscale pores. Such special GO/PDA morphology is particularly suited for high-efficient capture with enhanced surface area, which is different than any other reports.

Figure 2D:
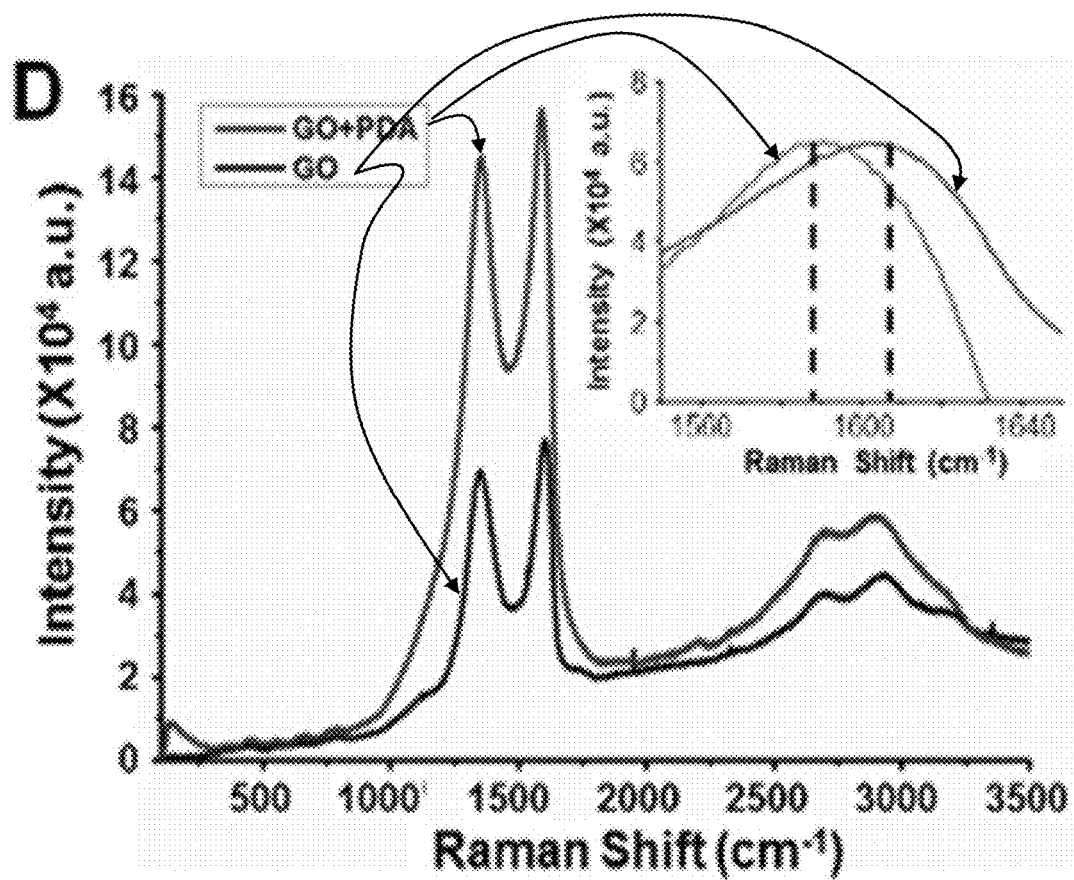
FIG. 2D includes a graph that shows the intensity versus ramen shift for Raman spectra of different chip coatings.

Such morphology obtained by microfluidic PDA coating is distinct from previously reported smooth PDA film coated on GO nanosheets and granular PDA morphology formed on various flat substrates using the benchtop methods. The further increased surface area and 3D porous structure of the GO-PDA coating is favorable to enhancing antibody immobilization and exosome-surface interactions for ultrasensitive immuno-capture and detection of exosomes. In addition to SEM imaging, PDA modification of the GO-coated surface was also confirmed by Raman spectroscopy. Both spectra in FIG. 2D exhibit characteristic peaks of GO at 1373 $cm^{-1}$ (D band) and 1592 $cm^{-1}$ (G band). Slight red shift of the G band was observed after PDA coating due to dopamine-induced GO reduction.

Figure 3A:
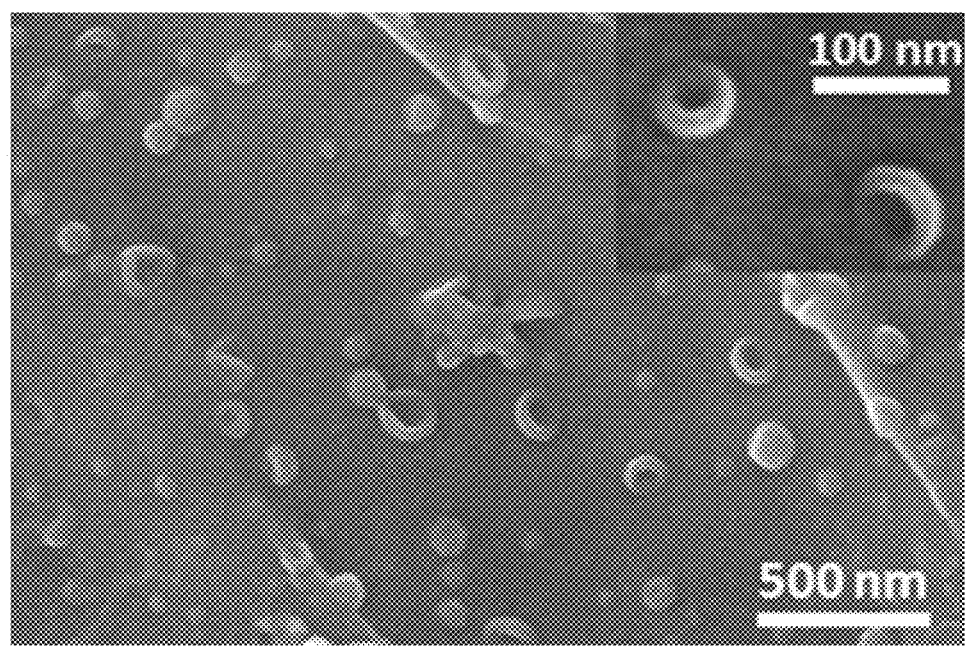
FIG. 3A includes an SEM image of densely captured COLO-1 cell-derived exosomes on the GO-PDA surface.

Using the GO-PDA nano-interface, an on-chip exosome ELISA was prepared using commercially available exosome standards purified from a culture medium of immobilize monoclonal antibodies (mAbs) in an oriented fashion to preserve the activity of antibodies. Data validated the immobilization approach by using a FITC-labeled CD81 mAb, and the data showed very strong fluorescent signal, indicating a high immobilization efficiency. Data showed that Protein G was first immobilized on the GO-PDA chip and FITC labeled anti-CD81 antibody was captured by Protein G. Data also showed that for a GO-PDA chip without immobilized Protein G, very low background was observed after flowing the FITC-labelled CD81 antibody (50 µg/mL) through the channel. This comparison verified that the antibody was immobilized through the Protein G-IgG interaction. This result also demonstrates that the PDA coating effectively suppresses fluorescence quenching by GO. A typical SEM image in FIG. 3A visualizes COLO-1 exosomes captured on the GO-PDA surface using an anti-CD81 mAb (e.g., targeting receptor). High exosome density on the nano-interface indicates the very good capture efficiency that the method provides. A round-cup morphology typical of exosomes was observed with the majority smaller than 150 nm, in contrast to a broader size range of the ultracentrifugation-purified exosomes measured by nanoparticle tracking analysis. The narrow size distribution observed by the solid-phase immuno-isolation is consistent with that of the bead-based method, suggesting an improved isolation specificity over the ultracentrifugation-based approach.

Figure 3B:
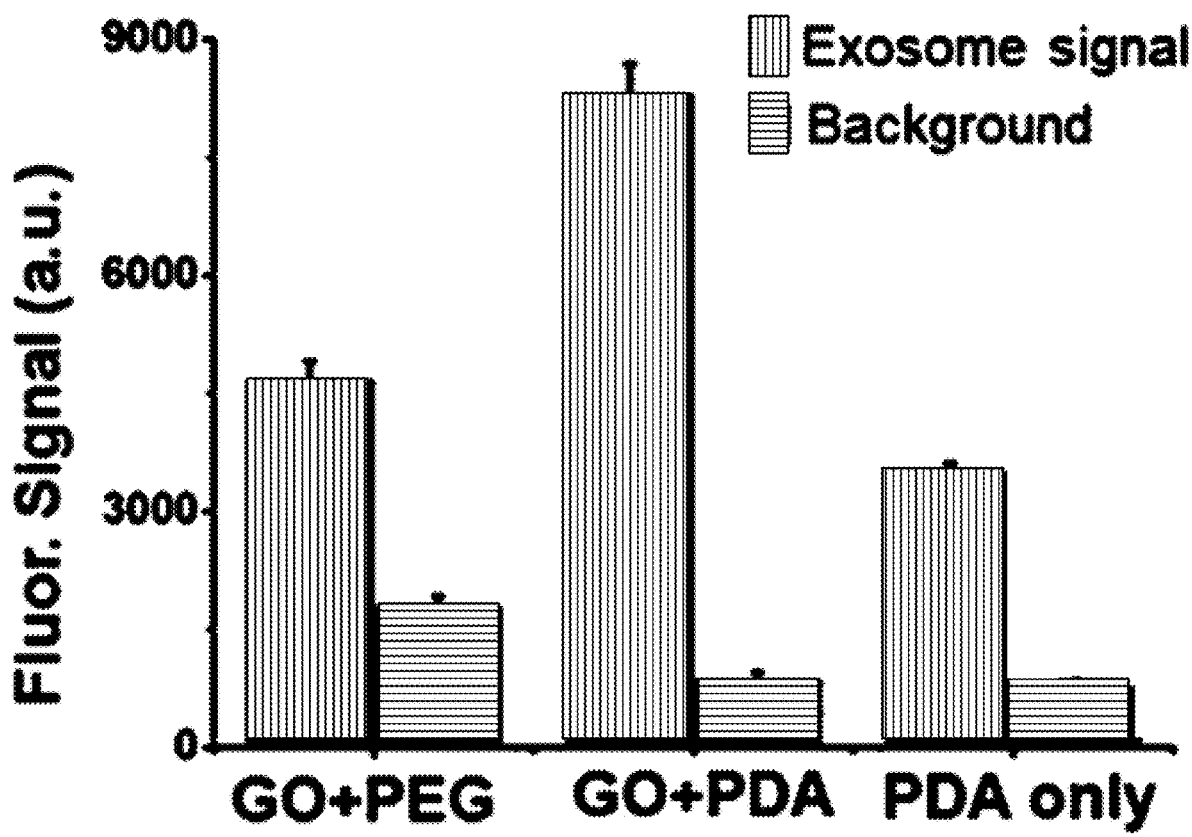
FIG. 3B includes a graph that illustrates the effects of different coatings on the microfluidic chip ELISA readout of exosomes and non-specific background, where exosome concentration was $5 \times 10^4$ $\mu L^{-1}$.
Figure 3C:
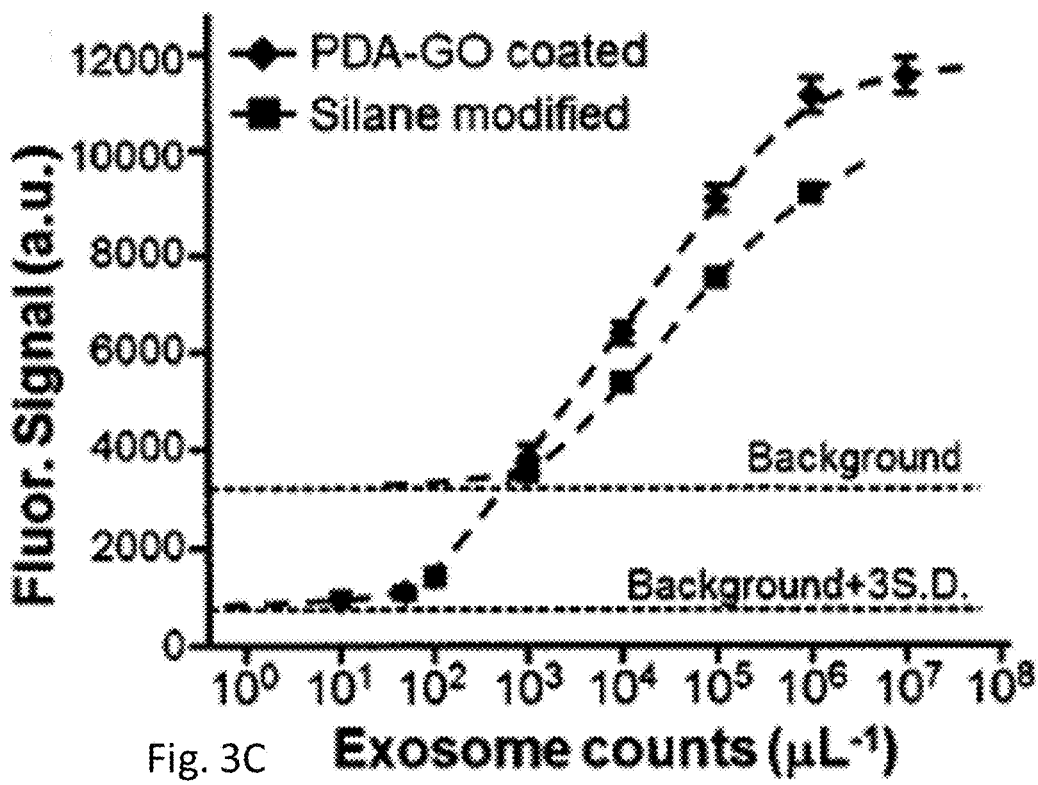
FIG. 3C includes a graph of fluorescent signal versus exosomal counts for comparing the GO-PDA interfaced and silane treated chips for exosome capture and detection.

To assess the effects of GO functionalization on exosome detection, studies compared the bioinspired PDA coating with the commonly used PEG modification and PDA only for detecting COLO-1 exosomes under the same assay conditions (see the Experimental Methods). It was seen that PDA functionalization of GO led to significantly enhanced assay signal and reduced non-specific background (FIG. 3B). Data shows that the fluorescence images and corresponding intensity plots of on-chip exosome ELISA readout and non-specific background using the microchips with different surface modifications. The data shows GO functionalized with PEG and GO functionalized with PDA. Exosome concentration was $5 \times 10^4$ $\mu L^{-1}$. Such improvement may be attributed to the collective effects of better surface coverage, porous structure, and larger surface area that the relatively thick PDA film affords, as opposed to the PEG monolayer formed on the GO surface. The capture device chip was assessed for exosome quantification using anti-CD81 mAb for capture and a mixture of detection mAbs specific to two common exosome markers (tetraspanins CD63 and CD81) and a tumor marker, Epithelial cell adhesion molecule (EpCAM). The calibration curve obtained under an optimized flow rate of 0.5 µL/min shows a very low limit of detection (LOD) of ~50 exosomes $L^{-1}$ with a 4-log dynamic range with (FIG. 3C). For comparison, parallel measurements with the chips modified by a common silanization method yielded lower response and much higher background, which results in a LOD on the order of $10^3$ $\mu L^{-1}$, 20-folds worse than that of the capture device chip (FIG. 3C). The comparative studies demonstrate the advantages of the GO-PDA nano-interface in substantially improving the analytical performance of microfluidics-based immuno-capture and detection of exosomes. The obtained sensitivity was nearly 100 times better than the previously reported microfluidic methods and $10^4$-fold higher than that of bench-top chemiluminescence ELISA. Moreover, the dynamic range was expanded by about two orders of magnitude.

Figure 3D:
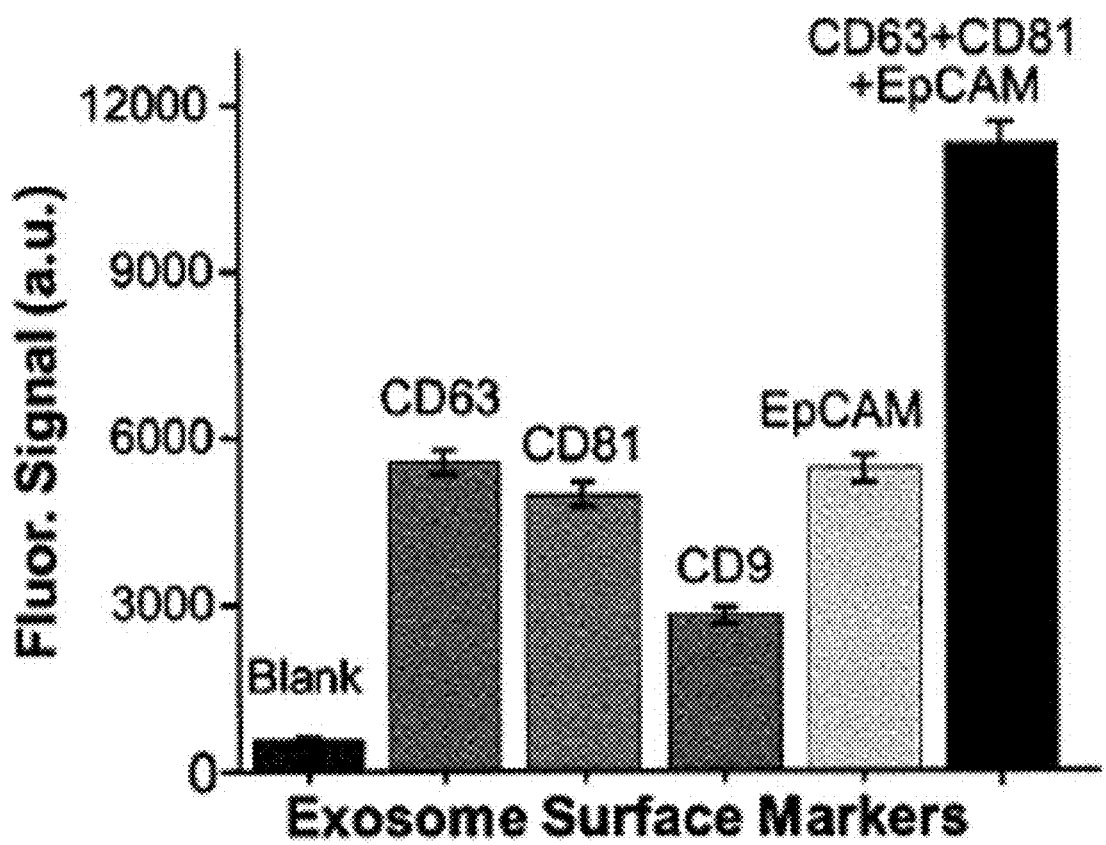
FIG. 3D includes a graph of the fluorescent signal for certain exosome surface markers, for surface protein profiling of exosomes ($10^6$ $\mu L^{-1}$) captured by anti-CD81 mAb in microfluidic chip with GO-PDA coated nanostructures.

Surface composition of exosomes is important to their transfer and functions and may provide specific biomarkers to diseases. To assess the method for quantitative surface profiling, studies measured individual COLO-1 exosome subpopulations expressing CD9, CD63, CD81 or EpCAM (FIG. 3D). Exosomal expression of these surface proteins appeared to be different with the CD9 level being much lower than others. This observed expression pattern for the tetraspanins (CD9, CD63, and CD81) is consistent with that characterized by the manufacturer of the exosome standards. Quantification of total exosomes captured by the CD81 antibody was attempted by using a mixture of detection antibodies. As expected, significantly higher fluorescent signal was obtained, which will improve the detection sensitivity for specifically captured exosome subpopulations. The data demonstrates the ability of the present technology for sensitive and quantitative exosome profiling to identify potential exosome fingerprints associated with diseases. The multichannel chip described herein allows for the measurements of a plurality of markers (e.g., five markers or other number) on one chip. The current platform can be readily scaled up to improve the multiplicity of exosome profiling.

Figure 3E:
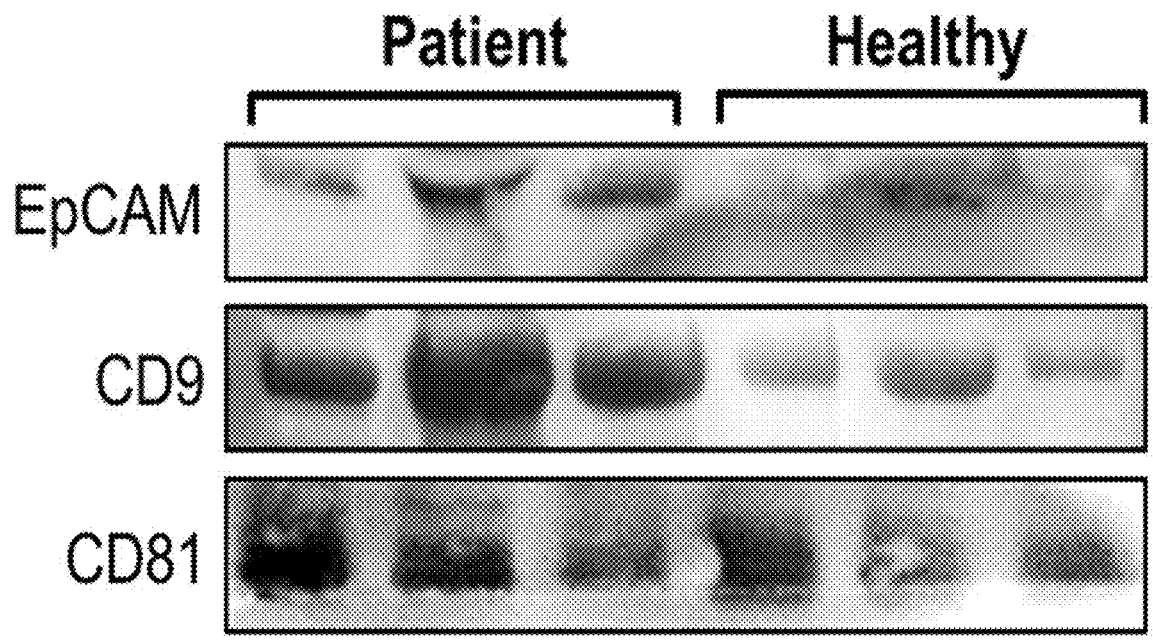
FIG. 3E shows Western blot analysis of expression of CD9, CD81 and EpCAM proteins in circulating exosomes purified from ovarian cancer and healthy plasma samples by ultracentrifugation for comparing on-chip results.
Figure 4A:
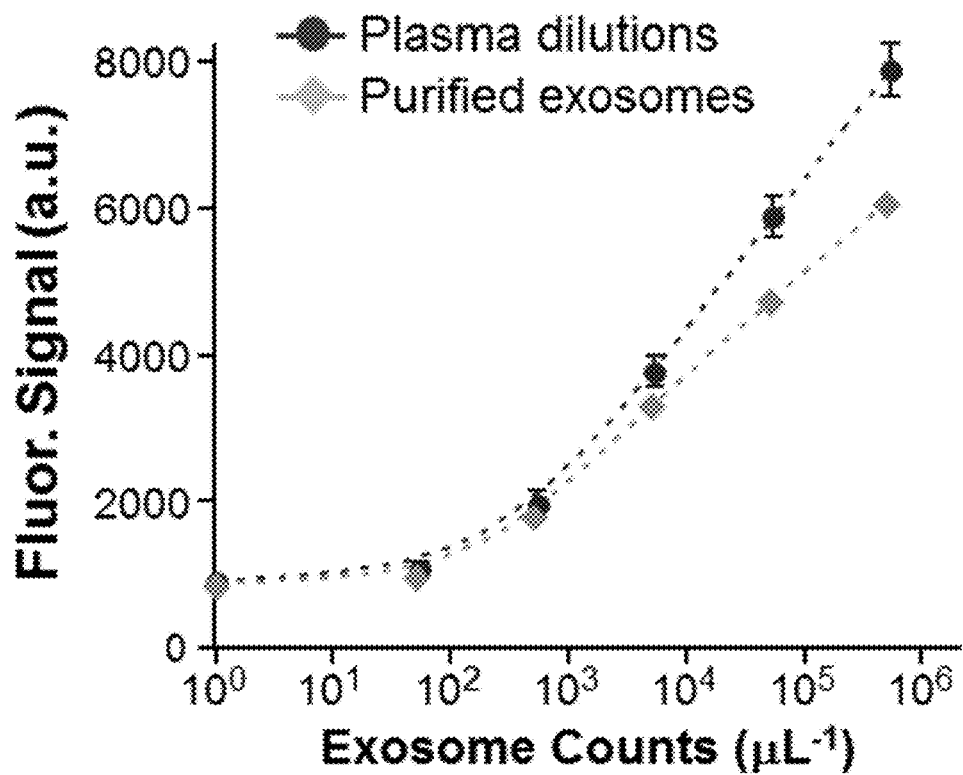
FIG. 4A includes a graph that shows the fluorescent signal versus exosome counts for calibration curves for detecting exosomes pre-purified and directly from patient plasma using GO-PDA nanochip.

To demonstrate the potential of the technology for clinical applications, circulating exosomes in clinical plasma samples collected from ovarian cancer (OvCa) patients were examined. Overexpression of total plasma-borne exosomes and certain subpopulations in ascites fluid has been reported in OvCa, providing a good disease model. Here we used anti-CD 81 mAb for capture and a cocktail of mixed mAbs against CD9, CD81 and EpCAM for quantitative detection. Expression of these markers in OvCa exosomes was confirmed by Western blot (FIG. 3E). For each subject tested here, exosomes were purified from a portion of the plasma sample by ultracentrifugation and quantified by NTA to determine the exosome concentration in plasma. The capture device platform was first calibrated using both pre-purified exosomes and plasma dilutions from the same patient (FIG. 4A). The system confers high sensitivity for detecting OvCa exosomes with a LOD consistent with that for COLO-1 cell-derived exosomes. Higher signals were detected for the plasma dilutions than pre-purified exosomes at the nominally same concentrations. This is owing to the fact that the ultracentrifugation-based protocols only recover a fraction of exosomes, thus underestimating true exosome levels in plasma. Previous studies have revealed that current sample preparation methods cause significant variation in exosome analysis. The data also underscores the importance of developing tools for direct analysis of clinical specimen to mitigate variance caused by multi-step sample processing.

Figure 4B:
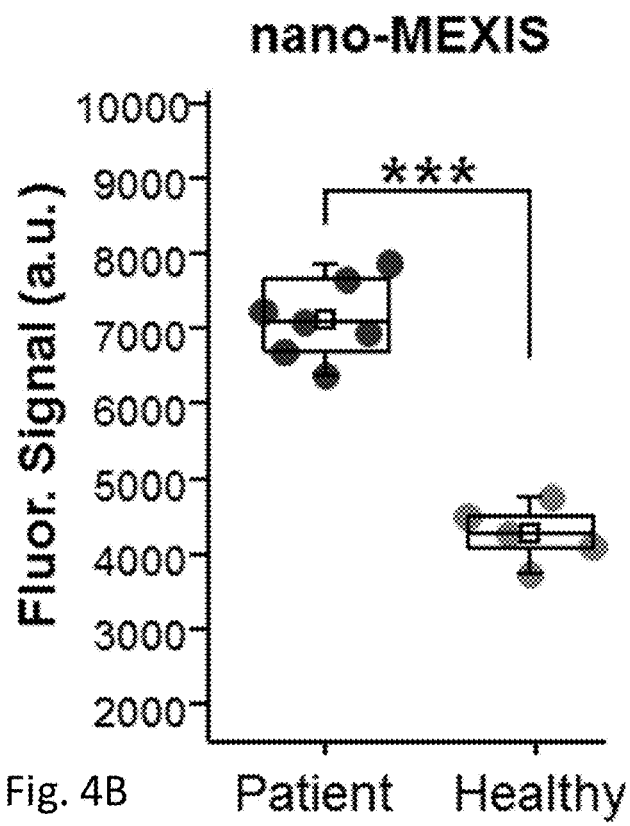
FIG. 4B includes a graph showing boxplots overlaid with dot plots for clinical sample analysis by the GO-PDA nano-capture device.
Figures 4C, 4D, 4E:
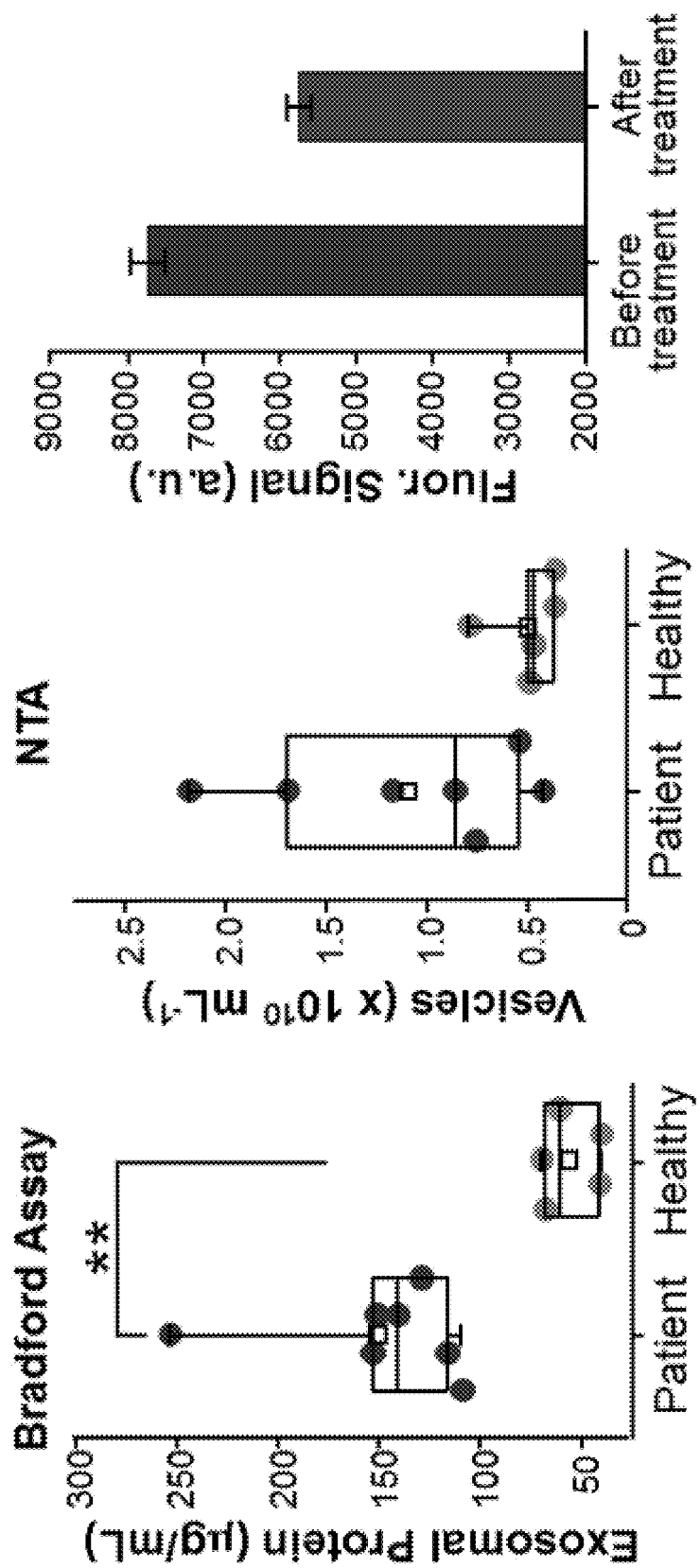
FIG. 4C includes a graph that shows a Bradford assay of total exosomal proteins for validating results from GO-PDA nanochip.
FIG. 4D includes a graph that shows NTA counting of exosomes purified from the same samples used in FIG. 4B for validating results from GO-PDA nanochip.
FIG. 4E includes a graph that shows the fluorescence signals of exosomes derived from ovarian cancer patient plasma before treatment and after treatment using GO-PDA nanochip.
Figure 4F:
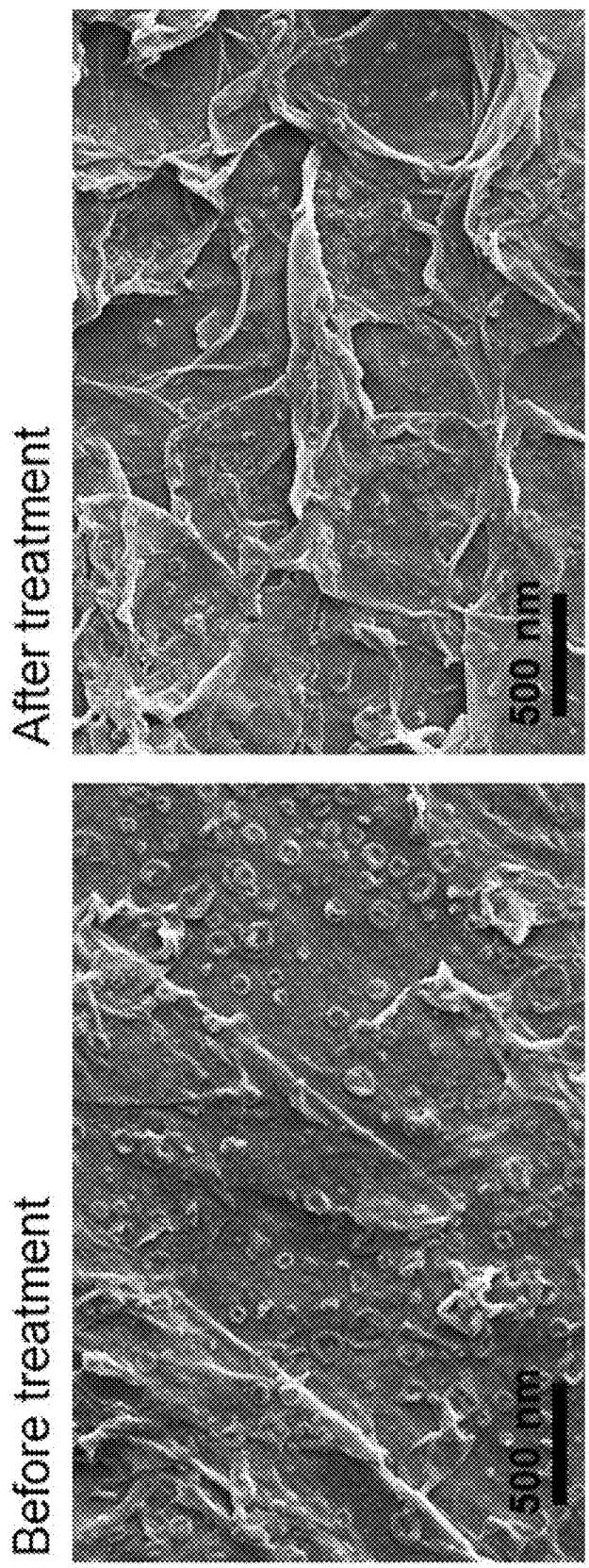
FIG. 4F shows micrographs before treatment and after treatment of an ovarian cancer (OvCa) patient, where SEM visualization of the chips right after the measurements shows a decreased density of captured exosomes from the post-treatment plasma.
Figures 4G, 4H:
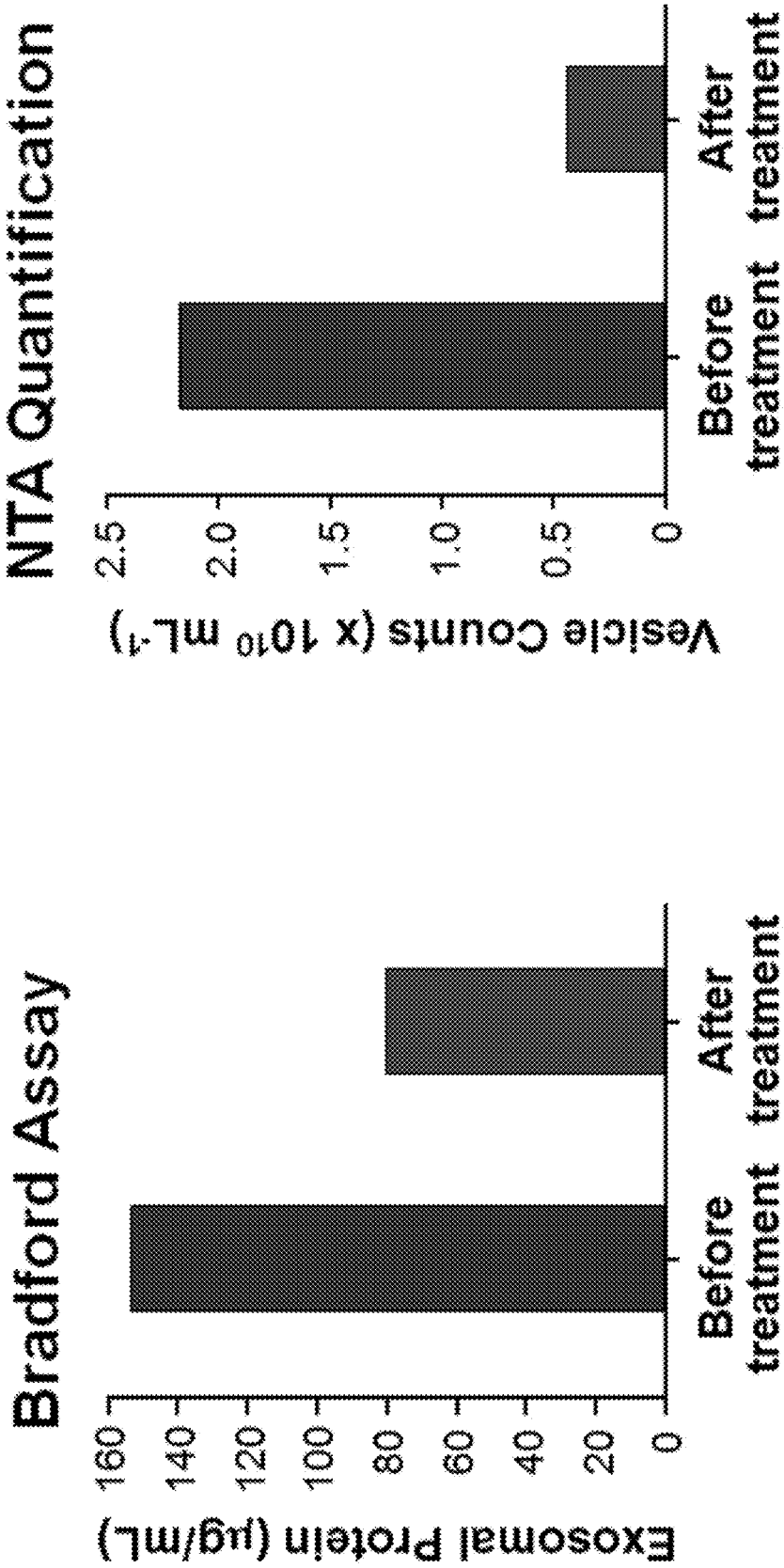
FIG. 4G includes a graph that illustrates a Bradford assay for exosomal protein before and after treatment of the OvCa patient, where comparison of the total exosomal protein level measured by the Bradford assay is shown between the plasma samples collected before and after treatment.
FIG. 4H includes a graph that illustrates an NTA quantification of vesicle counts before and after treatment of OvCa patient, where comparison exosome concentration quantified by NTA is shown between the plasma samples collected before and after treatment.

To this end, we analyzed plasma samples collected from seven OvCa patients and five healthy donors. A small volume of each plasma sample (2 µL) was diluted by 10 times for convenient injection into the channels. FIG. 4B shows that the OvCa group was well discriminated from the healthy controls ($p<0.001$), which could be attributed to the increased expression exosome concentration and the tumor marker EpCAM (FIG. 3E). The microfluidic measurements were further validated by the standard benchtop assays of exosomes purified and enriched from the same plasma samples. Significant exosome overexpression in OvCa was observed by the Bradford assay of total exosomal protein ($p<0.01$, FIG. 4C). NTA counting also detected an increase of the averaged exosome level in the patients; but a large variation observed for patient samples confounds the cancer diagnosis based on the exosome levels ($p=0.051$, FIG. 4D). In addition to cancer diagnosis, exosomes have been studied as a new tool for therapy monitoring. The system can be used to quantitatively detect the change of exosome expression in an OvCa patient in response to cancer treatment using the nano-IMEX chip. The system was able to detect a ~10-fold lower exosome level after the treatment than that at the time of diagnosis (FIG. 4E). SEM inspection of the chips after the assays showed a substantially lower density of exosomes captured from the post-treatment sample on the nano-interface than the pre-treatment sample (FIG. 4F), verifying the quantitative fluorescence detection by the exosome ELISA shown in FIG. 4E. The change in exosome expression observed by the microfluidic assay was further validated by the measurements of NTA and Bradford protein detection (FIGS. 4G and 4H). The data for ultrasensitive and specific exosome detection suggest the ability of the capture device platform for the applications of cancer diagnosis and monitoring treatment response.

In one embodiment, the present technology can include a microfluidic exosome sensing platform based on a bioinspired GO-PDA nano-interface. The data shows that the nano-interface greatly enhances the immuno-isolation efficiency while effectively suppressing the effects of fluorescence quenching by GO and non-specific interactions. This nano-interface enables the development of an ultrasensitive and specific ELISA assay for molecular analysis of exosomes. The data shows the applications of this capture device platform for molecular profiling and quantitative detection of exosomes purified from a colon cancer cell line or directly in plasma samples from ovarian cancer patients. The capture device is scalable for multiplexed analysis of exosomes and high-throughput screening of clinical samples. Therefore, this platform can provide a useful tool to facilitate exosome research and clinical utilities of exosomes for disease detection and treatment.

In one embodiment, the GO-PDA coating can be used to create a 3D nanostructured interface to enhance the targeting receptor to affinity capture of the target substance. In part, the 3D nanostructured interface can form due to PDA-induced spontaneous formation of a 3D nanostructured PDA morphology. This unique nanostructure greatly enhances the efficiency of exosome immuno-isolation when the targeting receptor targets the exosome, while at the same time effectively suppressing the non-specific background associations. Accordingly, the coating of GO and PDA linked to a targeting receptor can be used for an ultrasensitive target (e.g., exosome) detection.

In one aspect, the GO-PDA coating can be prepared via a surface coating method, which can be used to apply the GO-PDA coating to substantially any material surface, such as macroscopic fluid channel substrate or small particle (e.g., magnetic bead) surfaces.

Figure 9A:
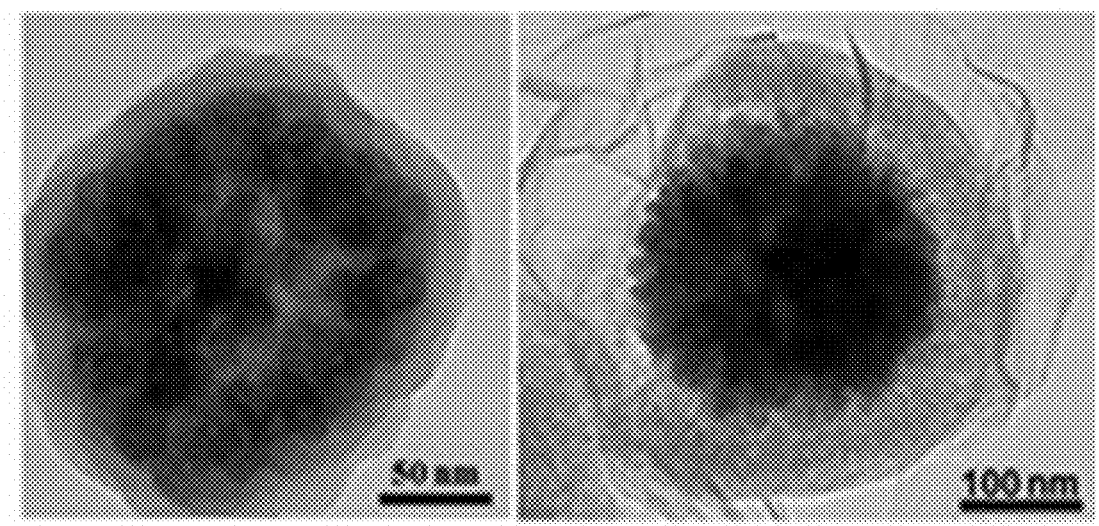
FIG. 9A shows a TEM of $Fe_3O_4@SiO_2$ magnetic beads (e.g., $Fe_3O_4$ core with $SiO_2$ shell) without (left) and with (right) covalently bonded graphene oxide.
Figure 9B:
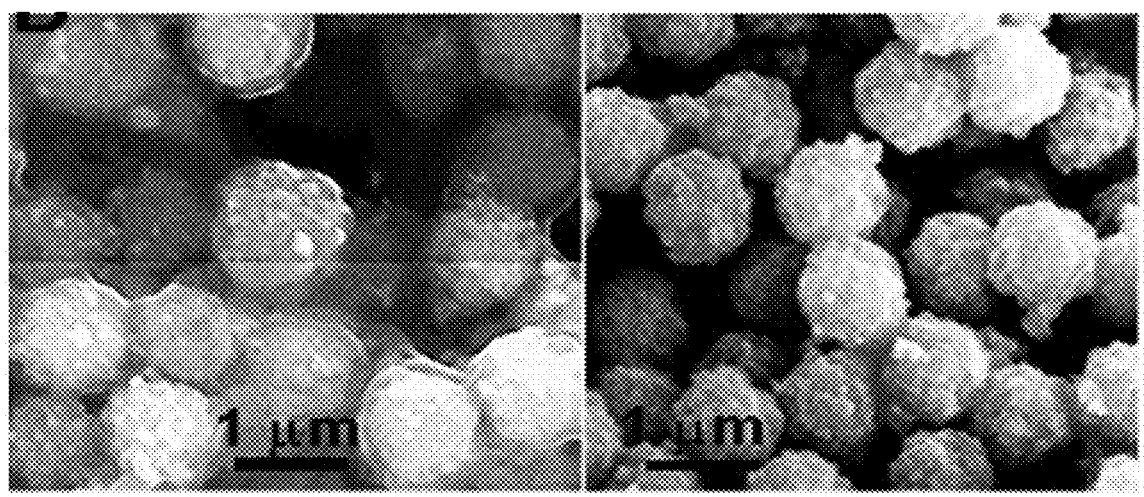
FIG. 9B shows SEM images for side by side comparison of nano-GO-PDA coated magnetic beads (left) with the bare beads (e.g., no nano-GO-PDA coating right).
Figure 9C:
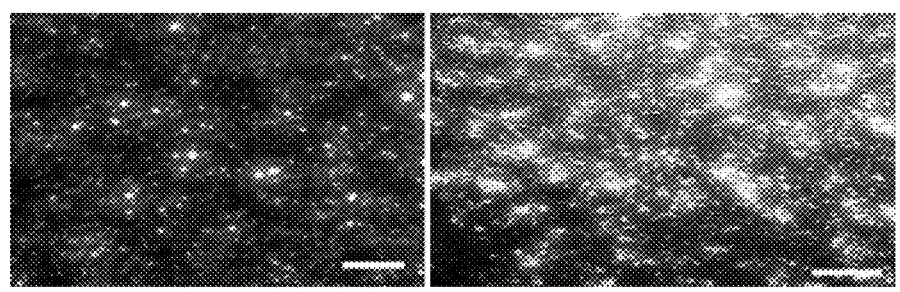
FIG. 9C shows the fluorescence microscopic image showing the BcMag™ streptavidin magnetic beads purchased from the BioClone for capturing FL-Biotin (left) and the fluorescence microscopic image showing the developed nano-GO-PDA coated magnetic beads for capturing FL-Biotin (right), where the scale bar is 30 μm.
Figure 10A:
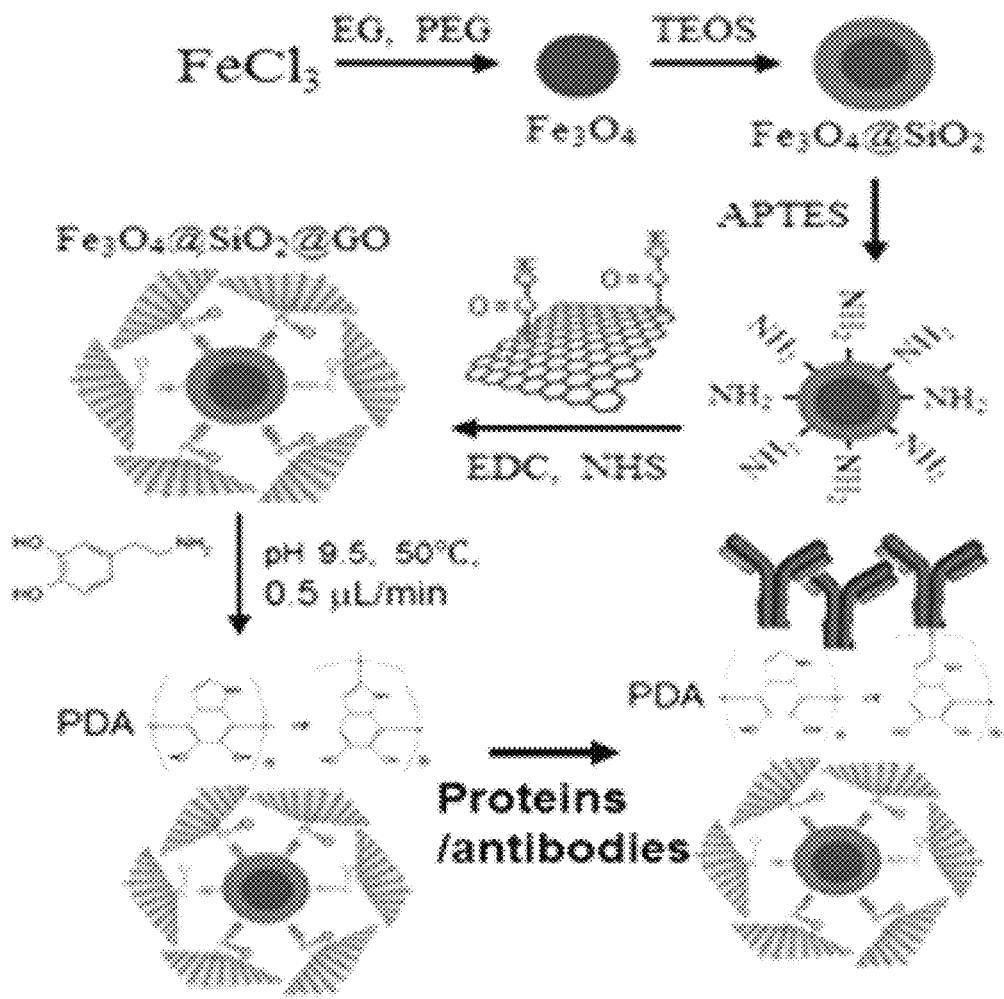
FIG. 10A shows a process for manufacturing the capture device of FIG. 1C.
Figure 10B:
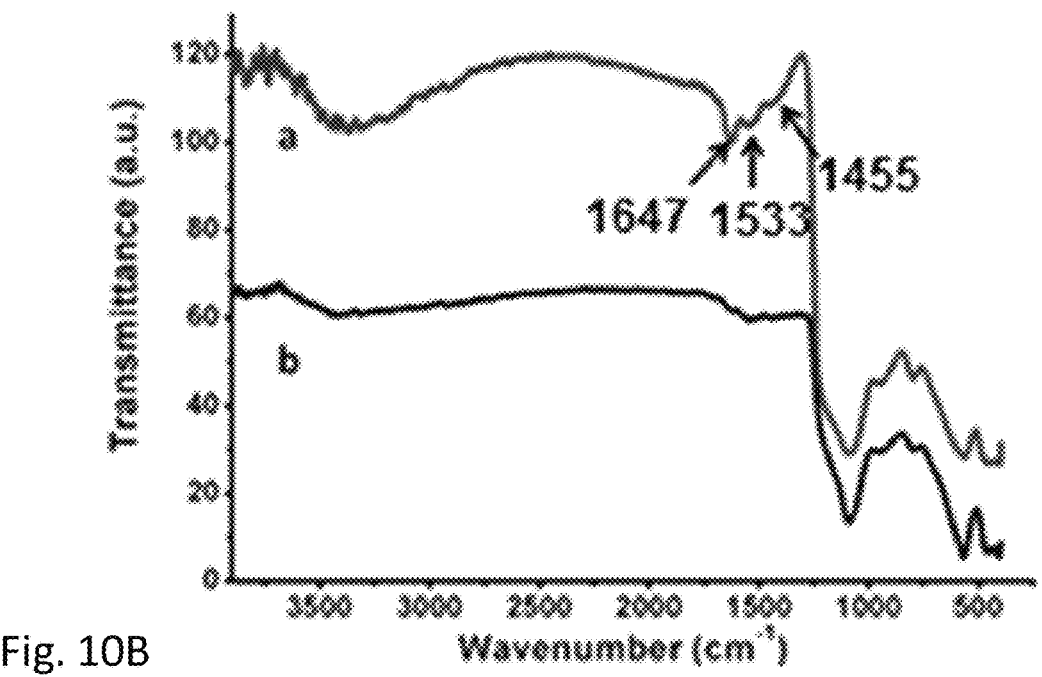
FIG. 10B includes a graph that shows the FT-IR spectra of graphene-oxide coated magnetic beads.

In one embodiment, this GO-PDA coating can be used to modify the surfaces of particles, such as magnetic beads, which can improve the isolation throughput and specificity to tumor cell-derived exosomes, or other biological substances (e.g., targets, target ligands). While workable, a non-covalently assembled nano-graphene coating can suffer from the instability in buffer solutions over time. As such, covalent bonding may be advantageous. FIG. 10A shows a method for forming the GO-PDA coated magnetic beads (e.g., nanoparticles). In the present method, encapsulated Fe3O4/SiO2 core-shell nanoparticles can be coated with graphene-oxide nanosheets via carboxamide covalent bonds formed by EDC/NHS chemistry and modified with (3-aminopropyl) triethoxysilane (APTES), which leads to substantially improved stability. APTES results in amine groups on the nanoparticles that can react with the carboxylic acid groups of the GO. As seen in FIG. 9A (TEM), nano-graphene coated magnetic particles showed much larger surface area. Covalent bonding was confirmed by FT-IR, as shown in FIG. 10B, showing three characteristic peaks which were undetected for the electrostatically assembled graphene magnetic particles: 1647 cm-1 (—CONH amide band I), 1533 cm-1 (—NH amide band II) and 1455 cm-1 (C—N stretch of amide). We also characterized the coating morphology by SEM as shown in FIG. 9B. An obvious thick layer can be observed from nano-graphene coated magnetic particles (left), compared to bare beads (right). The porous surface structure indicates the enhanced specific surface area which allows for immobilization of increased quantity of recognition antibodies. Proteins and antibodies conjugation can be simply introduced by polydopamine (PDA) chemistry with a deposition of a PDA layer on the GO surface by reacting the amine of the PDA with carboxylic acids of the GO such that the PDA polymers extend from the GO surface away from the particle core. The PDA conjugated to the GO still retains amine groups that can be used to react with the carboxylic acid groups of polypeptides, proteins, antibodies, and fragments thereof that are targeting receptors. This results in the PDA extending the targeting receptor away from the particle core. The deposition of PDA layers creates a 3D hydrophilic, nanostructured interface to enhance the affinity capture of the target. We compared the capture capacity of developed GO-PDA magnetic beads with commercial magnetic beads from BioClone (BcMag™ Streptavidin Magnetic Beads). Both streptavidin conjugated beads were incubated with fluorescence-labeled biotin under the same concentration and incubation time for assessing fluorescence intensity. Our developed GO-PDA streptavidin magnetic beads showed stronger fluorescence intensity which indicates a ~50% improvement on capture capacity (FIG. 9C). Much higher capture efficiency was observed from developed nano GO-PDA coated magnetic beads.

With regard to the PDA, the amine and catechol functional groups allow easy surface modification and bioconjugation with proteins, antibodies, and other biomolecules. The highly hydrophilic PDA coating possesses excellent biocompatibility and resistance to biofouling. The kinetics of PDA coating can be well controlled by tuning the reaction conditions such as pH, temperature, choice of oxidants and incubation time. The substrate, whether the channel surface or the bead surface that is functionalized with a GO-induced, nanostructured PDA film by microfluidic layer by-layer coating, permits simple covalent protein conjugation via PDA chemistry. In one aspect, the coating approach markedly expedites the PDA deposition kinetics, and can be complete within one hour, which could promote the greater application of this promising coating material.

Compared to other microfluidic methods and to benchtop ELISA, the GO-PDA interfaced nanosensing chip substantially improves the detection sensitivity and dynamic range, such as immuno-capture of exosomes at 50 $\mu L^{-1}$ (80 aM). Such high sensitivity enabled the quantitative detection of circulating exosomes directly from unprocessed plasma samples of minimal volume (2 $\mu L$), which is a key challenge in the clinical development of exosomal biomarkers. As a proof of concept, we used this nano-sensing chip to successfully distinguish ovarian cancer cases from healthy controls. These results demonstrate the potential of the capture device platform for exosome research and for clinical disease diagnosis and treatment, such as cancer as described herein or other diseases. Accordingly, the capture devices described herein can be used for targeting biomarkers, such as those of non-invasive diseases. Also, the capture devices can capture potential biomarkers for non-invasive disease diagnosis and monitoring of treatment response.

It was demonstrated that this nanostructured GO-PDA interface greatly improves the efficiency of exosome immuno-capture while effectively suppressing non-specific exosome adsorption. Based on this nano-interface, an ultrasensitive exosome ELISA assay was developed to afford a very low detection limit of 50 $\mu L^{-1}$ with a 4-log dynamic range, which is substantially better than the existing methods. As a proof of concept for clinical applications, we adapted this platform to discriminate ovarian cancer patients from healthy controls by quantitative detection of exosomes directly from 2 $\mu L$ plasma without sample processing. Thus, this platform could provide a useful tool to facilitate basic and clinical investigations of exosomes for non-invasive disease diagnosis and precision treatment.

These microsystems greatly improved the limit of detection down to ~106 vesicles/mL and substantially reduced sample consumption and analysis time. Concentrations of EVs, including exosomes, have been reported to vary dramatically in various biological fluids, such as from 104 to 1010 $mL^{-1}$ in plasma and even lower in cerebrospinal fluid (CSF).

The capture device may also be used in highly sensitive exosomes for various studies, such as single-vesicle profiling of exosomal heterogeneity 21 and single-cell analysis of exosome secretion, to better elucidate exosome functions.

It was found that functionalization of microfluidic devices with the GO-PDA-Receptor coatings can improve the capture of circulating tumor cells (CTCs) with or even without using affinity capture probes.

In one aspect, the Y-shaped microposts (e.g., FIG. 5) functionalized with a GO-induced, nanostructured PDA film by microfluidic layer-by-layer coating, permits simple covalent protein conjugation via PDA chemistry. These Y-shaped microposts having the GO-PDA-Receptor can be used for various methods of capturing targets from samples, such as biological samples.

The GO-PDA-Receptor provides high sensitivity enabled quantitative detection of circulating exosomes directly from unprocessed plasma samples of minimal volume (2 µL), which can be used to capture exosomal biomarkers.

In one embodiment, the present technology includes methods, systems, devices or kits that have a substrate with the GO-PDA-Receptor. Kits can have the substrate with the GO-PDA-Receptor or components thereof with instructions for preparation of the substrate with the GO-PDA-Receptor. Kits may also include reagents for performing capture methods described herein. The substrate with the GO-PDA-Receptor can be used in methods for diagnosing or aiding in a physician's diagnosis of a condition, where such a method can include testing a biological sample comprising or suspected of comprising exosomes. The substrate may be a flow channel or magnetic beads, or the like, to capture the targeted exosomes from the sample. The substrate with the GO-PDA-Receptor can be used for testing for the presence or absence of exosomes that comprise one or more markers of a cancer, or other disease. The substrate with the GO-PDA-Receptor can form a complex with one or more captured agents (e.g., exosomes) having a surface marker in non-covalent association with the receptor, wherein the captured agent (e.g., exosome) is reversibly or irreversibly attached. The complex can be formed by contacting a biological sample from an individual with a capture device as generally depicted and/or described herein.

In one embodiment, the GO includes a carboxylic acid functional group, but is devoid of a hydroxyl and/or oxirane functional group. In one aspect, the methods described herein for forming the capture device can include obtaining graphene and oxidizing the graphene into graphene oxide (GO).

In one embodiment, the substrate surface includes amine groups that can react with the carboxylic acid functional groups of the GO to form amide bonds covalently bonding the substrate surface to the GO. In one aspect, the methods described herein for forming the capture device include obtaining a surface, such as glass, silicone, polydimethylsiloxane, (e.g., PDMS), or other, and reacting the surface to form a functional group. The functional group on the surface may be an amine or other nitrogen containing functional group that can react with carboxylic acid of the GO. In one aspect, the methods described herein for forming the capture device include reacting the reactive amine functional group of the surface with the carboxylic functional group of the GO.

In one embodiment, the PDA may include reactive amine groups, such as amine groups that are free or within the cyclic group as shown that can react with carboxylic acids. In one aspect, the method includes synthesizing the PDA, such as with the steps described herein or generally known. In one aspect, the methods described herein for forming the capture device include reacting the reactive amine functional group of the PDA with the carboxylic functional group of the GO. In one aspect, the methods described herein for forming the capture device include reacting the reactive amine functional group of the PDA with the carboxylic functional group of a targeting receptor, such as on an amino acid, C-terminus, or elsewhere in the peptide, polypeptide, antibody, or fragment thereof.

In one embodiment, the capture device can be used to isolate the targeted biological substance from a biological sample, such as urine, blood, CFS, plasma, or other body fluid or extract thereof. The sample can be contacted with the capture device so that the targeted biological substance associates with the targeting receptor. The sample is then removed from the capture device, or the capture device is removed from the sample. The capture device can be analyzed to determine the presence of the targeted biological substance, qualitatively analyze the targeted biological substance, or quantitatively analyze the targeted biological substance. In one aspect, such capturing of the targeted biological substance is for diagnostics, such as diagnosis a disease state by the presence of the targeted biological substance indicating the disease state. In one aspect, such capturing of the targeted biological substance can be used in analytics and assays that are not diagnostic, which can include isolating the targeted biological substance from a sample for various purposes.

In one embodiment, the technology includes an automated system that can include the capture device for isolating the targeted biological substance from a sample.

In one embodiment, the graphene-oxide is non-covalently associated with a copper or stainless steel substrate surface.

In one embodiment, the PDA forms a porous structure on the GO, with PDA polymers extending from the GO surface. In one aspect, an end of the PDA polymer, such as a linear PDA polymer, can be coupled to the GO, such that the plurality of PDA polymers form the porous structure or 3D structure with recesses and protrusions as shown in the figures. In an example, the PDA polymers extend in a finger-like manner from the GO. The targeting receptor may be attached to the other end of the PDA or at any amine along the length of the PDA polymer. In one instance, the PDA of a capture device can have at least two or a plurality of different types of targeting receptors coupled therewith.

Experimental Methods

Reagents and materials. 3-Aminopropyl triethoxysilane (APTES), (3-Mercaptopropyl) trimethoxysilane (3-MPS), 4-Maleimidobutyric acid N-hydroxysuccinimide ester (GMBS), N-(3-Dimethylaminopropyl)-N'-ethylcarbodiimide hydrochloride (EDC), N-Hydroxy-succinimide (NHS), Tris(hydroxymethyl) aminomethane (Tris), Dopamine hydrochloride and graphene oxide were purchased from Sigma-Aldrich; Recombinant Protein G, human block IgG were ordered from Thermo Scientific); Streptavidin conjugated β-Galactosidase (SβG), Fluorescein di-β-D-galactopyranoside (FDG) were purchased from Life Technology. The antibodies used in our experiments are listed in Table 1 below. 1× phosphate-buffered saline solution (PBS) was from Mediatech, Inc.; all other solutions were prepared with deionized water (18.2 MV-cm, Thermo Scientific). SβG and FDG were dissolved in the PBS working solution (PBSW) at pH 7.4 which contains 0.5 mM DL-dithiothreitol solution (Sigma-Aldrich), 2 mM $MgCl_2$ (Fluka Analytical), and 5% bovine serum albumin (BSA) (Sigma-Aldrich).

TABLE 1

The list of monoclonal antibodies used in this research.

| No. | Target | Vendor | Catalog No. | Clone |
|---|---|---|---|---|
| 1 | CD 9 (biotin, human) | Ancell | 156-030/mono mouse | C3-3A2 |
| 2 | CD 63 (biotin, human) | Biolegend | 353018/mono mouse | H5C6 |
| 3 | CD 81 (biotin, human) | Ancell | 302-030/mono mouse | 1.3.3.22 |
| 4 | CD 81 (human) | Ancell | 302-820/mono mouse | 1.3.3.22 |
| 5 | CD 81 (FITC, human) | Ancell | 302-040/mono mouse | 1.3.3.22 |
| 6 | EpCAM (biotin, human) | Abcam | ab187270/mono mouse | MOC-31 |

Microfabrication and functionalization of the GO-PDA microchips. The silica mold for the PDMS chip was prepared using the standard photolithography method. Briefly, a silica wafer was cleaned with piranha solution and then the channel structure with 30 μm thickness was patterned on the surface of the silica wafer by spin-coating SU-8 2010 at 4500 rpm for 60 s. The wafer was prebaked at 65° C. for 2 min and at 95° C. for 4 min and exposed to UV for 9 s for a total energy dose of 110 mJ cm$^{-2}$. The wafer was then post-baked at 65° C. for 1 min and 95° C. for 4 min, followed by a 2 min development and hard-baking at 165° C. for 30 min. Before making the PDMS chips, all silica molds were treated with trimethylchlorosilane by gas phase silanization under vacuum for 4 h. For PDMS layer, 30 g PDMS mixture at a 10 (base material):1 (curing agent) ratio was poured on the mold and cured in the oven at 70° C. for 4 h. PDMS pieces were cut and peeled off from the mold and holes were punched. After treated with UV Ozone (UVO-Cleaner®42, Jelight Company Inc.), the glass slide and PDMS slab were bonded permanently.

For surface modification of the PDMS chips, 5% APTES in anhydrous ethanol was pumped through the channels for 1 h at room temperature. After washing with water for three times, GO solution (0.5 mg/mL) was flowed through the channels and GO nanosheets were adsorbed onto the APTES coated surface via electrostatic interaction. Subsequent PDA coating was carried out on a 50° C. heating plate. Dopamine was dissolved in 10 mM Tris buffer (2 mg/mL, pH 9.5) and flowed through the GO coated channels under a constant flow rate (0.5 μL/min) using a syringe pump. Upon the completion of coating, the channel was washed with water carefully to remove excess PDA solution. For antibody immobilization, the coated channel was filled with Protein G in PBS buffer (0.2 mg/mL) and reacted for 16 h at room temperature. Excess proteins were washed away and capture antibody CD81 (20 μg/mL) was immobilized via Protein G-IgG interaction. Prior to use, the prepared GO-PDA microchip was blocked with 5% BSA and 1% human IgG for 1 h. To assess the immobilization performance, we used FITC labelled CD81 (50 μg/mL) to react with Protein G following the same process and then measured the resultant fluorescence signal. The prepared GO-PDA microchip was stored in a 4° C. refrigerator for further usage. Also, any protein, polypeptide, antibody, or fragment thereof that is a targeting receptor that can target and bind with the target ligand can be conjugated to the PDA as described herein.

Preparation of microchips in control experiments. To modify the GO-coated chips with PEG, with the assistance of EDC and NHS, the carboxyl groups of GO reacted with amine groups of $NH_2$-PEG-$NH_2$ (MW3400) (Laysan Bio Inc.). After PEG functionalization, Protein G was immobilized onto the GO surface with glutaraldehyde as the linker for antibody immobilization. The flat microchips without the GO-PDA treatment were surface functionalized using a common silanization-based approach according to the previous report. Briefly, the PDMS chips were treated first with (3-Mercaptopropyl) trimethoxysilane and then with GMBS. At last Protein G (0.2 mg/mL) was immobilized through the reaction between amine group and thiol group.

Raman spectroscopic characterization of the GO-PDA microchips. Raman spectrum measurements were performed with a Renishaw Invia Raman microscope system. A Spectra Physics argon-ion laser operating at 633 nm was used as the excitation source with a laser power of 3 mW. The Rayleigh line was removed from the collected Raman scattering using a holographic notch filter in the collection path. All SERS spectra reported here were the results of a single 10-s accumulation.

COMSOL Simulation. Two-dimensional finite element simulations of fluid flow inside the Y-shaped micropost array were performed by using COMSOL Multiphysics 5.1 with the Microfluidics Module (Comsol Inc.). Navier-Stokes equations for incompressible fluid flow were used with an inlet flow rate of 1 μL/min. No slip boundary condition was applied for all walls.

SEM imaging of surface-captured exosomes. For SEM measurements, the captured exosomes were fixed with 2.5% glutaraldehyde in a PBS buffer for 30 minutes and then rinsed for 3×5 minutes. The samples were post-fixed for 15 minutes in 1% osmium tetroxide and rinsed 10 minutes with water. The samples were dehydrated in a graded series of ethanols (30%, 50%, 70%, 95% and 100%) for 2×10 min at each step. The samples were then coated with gold using a high resolution ion beam coater and examined with FEI Versa 3D Dual Beam scanning electron microscope at the KU Microscopy and Analytical Imaging Laboratory.

Characterization of the chip using colon cancer exosome standards. Lyophilized exosome standard from COLO-1 cell culture supernatant (2×30 μg vials) was purchased from HansaBioMed, Ltd (Tallinn, Estonia). Exosome pellets were suspended in water and measured by NTA to determine the concentration of exosomes. The stock solution was aliquoted and stored at −80° C. Exosome standards for calibration experiments were freshly prepared from the aliquots by serial 10× dilution in a PBS buffer. For exosome analysis, 20 μL of the standards with different concentrations were pumped into the microchips using a 50 μL microsyringe and a syringe pump. After exosome capture, unbound exosomes were washed away with 20 μL PBS buffer. The on-chip captured exosomes were then recognized by a mixture of three biotinylated detection antibodies specific to CD63, CD81 and EpCAM (20 μg/mL each). The chip was washed with 10 μL PBS again and 7.5 μL streptavidin conjugated β-galactosidase (SβG) prepared in PBSW buffer (20 ng/mL) was introduced as the reporter enzyme for chemifluorescence detection. Subsequently, 7.5 μL di-β-D-galactopyranoside (FDG) (500 μM) in PBSW buffer was also introduced and reacted for 0.5 hrs in the dark. Fluorescence images were acquired using an inverted epifluorescence microscope (Motic AE31) equipped with a 20× (N.A.=0.35) Zeiss objective and a scientific CMOS camera (OptiMOS, QImaging) controlled by an open source software Micro-Manager 1.4. Digital images from different areas in a chip were processed and analyzed using ImageJ to obtain the averaged fluorescence intensity.

Capture and detection of clinical plasma samples. Human plasma samples were collected from healthy donors and ovarian cancer patients. Following the protocols that we reported in the previous studies, circulating exosomes in plasma samples were purified by differential ultracentrifugation and then characterized by NTA sizing and quantification, Bradford assay, and Western blot. The purified exosomes in PBS were stored in a −80° C. freezer (Thermo Scientific).

In direct analysis of plasma samples from patients and healthy controls, we diluted a 2 μL plasma sample by 10 times with PBS buffer first to reduce the solution viscosity and ease injection using a 50-μL microsyringe. Then 20 μL of the diluted plasma samples were injected through the GO-PDA microchips for exosome capture and fluorescent ELISA detection using a syringe pump. The processes for exosome assay and data acquisition were the same as that for colon cancer exosome standards discussed above. In this case, we used CD81 mAb for capture and a cocktail of biotinylated mAbs (20 μg/mL each) for CD9, CD81 and EpCAM as detection antibody. To statistically assess the data from the patient and healthy control groups, a two-sample Welch's t-test with unequal variances was performed and all P-values, unless otherwise specified, were calculated at a significance level of 0.05.

Accordingly, the present invention can include a microscale fast deposition of PDA covalently formed on the surface of GO to create an unique 3D monolith-like structure with micro-/nanoscale pores. Such special GO/PDA morphology is particularly suited for high-efficient capture with enhanced surface area, which is different than any other reports.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

The invention claimed is:

1. A graphene-oxide coated particle for capturing a biological substance, the particle comprising:
    a core particle having a surface;
    a graphene-oxide-layer coating said core particle, said graphene-oxide layer comprising graphene-oxide nanosheets, said graphene-oxide nanosheets being covalently bonded to the particle surface;
    at least one polydopamine polymer coupled with the graphene-oxide nanosheets; and
    at least one targeting receptor coupled to the at least one polydopamine polymer, wherein the targeting receptor is capable of targeting and binding with a target biological sub stance.

2. The graphene-oxide coated particle of claim 1, wherein the core particle includes a functional group covalently coupled with a functional group of the graphene-oxide layer to form the covalent bond between the surface and graphene-oxide nanosheets.

3. The graphene-oxide coated particle of claim 1, wherein the graphene-oxide nanosheets include a functional group that is covalently coupled with a functional group of the at least one polydopamine polymer to form a covalent bond between the graphene-oxide nanosheets and polydopamine polymer.

4. The graphene-oxide coated particle of claim 1, wherein the at least one polydopamine polymer includes a functional group that is covalently coupled with a functional group of the at least one targeting receptor to form a covalent bond between the polydopamine polymer and targeting receptor.

5. The graphene-oxide coated particle of claim 1, wherein the targeting receptor is an antibody or fragment thereof.

6. The graphene-oxide coated particle of claim 1, wherein the target biological substance is an exosome.

7. The graphene-oxide coated particle of claim 1, wherein the core particle is a core/shell magnetic particle having a magnetic core and a functionalized shell.

8. The graphene-oxide coated particle of claim 1, wherein the graphene-oxide nanosheets are covalently bonded to the at least one polydopamine polymer; and wherein the at least one polydopamine polymer is covalently bonded to the at least one targeting receptor.

9. The graphene-oxide coated particle of claim 1, comprising the target biological substance bound to the targeting receptor.

10. The graphene-oxide coated particle of claim 1, wherein said particle is a magnetic bead.

11. The graphene-oxide coated particle of claim 1, wherein said graphene-oxide layer comprises a plurality of said graphene-oxide nanosheets covalently bonded to said substrate surface, said graphene-oxide nanosheets having a plurality of polydopamine polymers coupled thereto.

12. The graphene-oxide coated particle of claim 11, wherein each polydopamine polymer extends from the graphene-oxide layer away from the particle.

13. The graphene-oxide coated particle of claim 11, wherein said plurality of polydopamine polymers form a layer having a 3-dimensional, porous morphology on said graphene-oxide layer.

14. A method of capturing a target biological substance, the method comprising:
    providing the graphene-oxide coated particle of claim 1; and
    contacting a sample with the graphene-oxide coated particle such that the target biological substance associates with the targeting receptor.

15. The method of claim 14, detecting the presence of the target biological substance being bound with the targeting receptor.

16. The method of claim 14, comprising one of:
    removing the graphene-oxide coated particle from the sample; or
    removing the sample from the graphene-oxide coated particle.

17. The method of claim 14, comprising dissociating the target biological substance from the targeting receptor.

18. The method of claim 15, comprising qualitatively or quantitatively determining an amount or relative amount of the target biological substance in the sample.

19. A method of determining a disease state in a subject, the method comprising:
    providing the graphene-oxide coated particle of claim 1;
    obtaining a sample from the subject;
    contacting the sample with the graphene-oxide coated particle;
    and
    detecting the presence of the target biological substance in the sample, wherein if the target biological substance binds with the targeting receptor, the target biological substance is present in the sample, or if the target biological substance does not bind with the targeting receptor, the target biological substance is absent in the sample to thereby determine the disease state in the subject.

* * * * *